US010555532B2

(12) United States Patent
Thompson et al.

(10) Patent No.: US 10,555,532 B2
(45) Date of Patent: Feb. 11, 2020

(54) PLANT GROWTH-PROMOTING BACTERIA AND METHODS OF USE

(71) Applicant: Spogen Biotech Inc., St. Louis, MO (US)

(72) Inventors: Brian Thompson, Creve Coeur, MO (US); Katie Thompson, Creve Coeur, MO (US); Brittany Angle, Columbia, MO (US)

(73) Assignee: Spogen Biotech Inc., St. Louis, MO (US)

(*) Notice: Subject to any disclaimer, the term of this patent is extended or adjusted under 35 U.S.C. 154(b) by 359 days.

(21) Appl. No.: 14/775,858

(22) PCT Filed: Mar. 17, 2014

(86) PCT No.: PCT/US2014/030726
§ 371 (c)(1),
(2) Date: Sep. 14, 2015

(87) PCT Pub. No.: WO2014/145883
PCT Pub. Date: Sep. 18, 2014

(65) Prior Publication Data
US 2016/0262402 A1   Sep. 15, 2016

Related U.S. Application Data

(60) Provisional application No. 61/790,476, filed on Mar. 15, 2013.

(51) Int. Cl.
A01N 63/02       (2006.01)
C12R 1/01        (2006.01)
C12R 1/085       (2006.01)
A01N 63/00       (2020.01)
A01H 3/00        (2006.01)
C12R 1/05        (2006.01)
C12R 1/07        (2006.01)
C12R 1/125       (2006.01)

(52) U.S. Cl.
CPC .............. *A01N 63/00* (2013.01); *A01H 3/00* (2013.01); *A01N 63/02* (2013.01); *C12R 1/01* (2013.01); *C12R 1/05* (2013.01); *C12R 1/07* (2013.01); *C12R 1/075* (2013.01); *C12R 1/085* (2013.01); *C12R 1/125* (2013.01)

(58) Field of Classification Search
CPC ........ A01N 25/00; A01N 63/02; A01N 63/00; A01H 3/00; C12R 1/01; C12R 1/05; C12R 1/07; C12R 1/075; C12R 1/085; C12R 1/125
USPC ................................................ 504/100, 117
See application file for complete search history.

(56) References Cited

U.S. PATENT DOCUMENTS

| 5,503,652 | A | 4/1996 | Kloepper et al. |
|---|---|---|---|
| 6,309,440 | B1 | 10/2001 | Yamashita |
| 7,393,678 | B2 | 7/2008 | Triplett et al. |
| 9,573,980 | B2 | 2/2017 | Thompson et al. |
| 9,826,743 | B2 | 11/2017 | Curtis et al. |
| 9,845,342 | B2 | 12/2017 | Thompson et al. |
| 9,850,289 | B2 | 12/2017 | Thompson et al. |
| 10,092,009 | B2 | 10/2018 | Thompson et al. |
| 2003/0228679 | A1 | 12/2003 | Smith et al. |
| 2008/0248953 | A1* | 10/2008 | Smith ...................... A01H 3/00 504/100 |
| 2009/0192040 | A1* | 7/2009 | Grobler .................. A01N 25/04 504/313 |
| 2014/0274691 | A1 | 9/2014 | Thompson et al. |
| 2014/0342905 | A1 | 11/2014 | Bullis et al. |

FOREIGN PATENT DOCUMENTS

| CA | 2146822 A1 | 10/1995 |
|---|---|---|
| CN | 10-2031231 A | 4/2011 |
| EP | 1 465 980 B1 | 8/2010 |
| IN | 801/CHE/2011 | 7/2014 |
| IN | IN801/CHE/2011 * | 7/2014 |
| JP | H1-305004 A | 12/1989 |
| JP | H10-203917 A | 8/1998 |
| JP | 2002-354943 A | 12/2002 |
| JP | 2005-298409 A | 10/2005 |
| KR | 10-2011-0102787 A | 9/2011 |
| RU | 2 313 941 C2 | 1/2008 |
| WO | 02/45513 A2 | 6/2002 |
| WO | 2009/056494 A2 | 5/2009 |
| WO | 2011/121408 A1 | 10/2011 |
| WO | 2013/090628 A1 | 6/2013 |
| WO | WO 2013090628 A1 * | 6/2013 ............. A01N 63/00 |

(Continued)

OTHER PUBLICATIONS

Pereira et al., "Compatibility among fungicide treatments on soybean seeds through film coating and inoculation with Bradyrhizobium strains", 2010, Capa, v. 32,n. 4,abstract.*

(Continued)

*Primary Examiner* — Johann R Richter
*Assistant Examiner* — Courtney A Brown
(74) *Attorney, Agent, or Firm* — Stinson LLP

(57) ABSTRACT

The present invention generally relates to bacteriologically pure bacterial cultures of novel strains of plant growth-promoting bacteria, and inoculums comprising the same. The invention is also directed to plant seeds coated with the inoculums, kits comprising the inoculums and methods for stimulating plant growth by applying the biologically pure bacterial culture or the inoculum to a plant, plant seed, or plant growth medium.

58 Claims, No Drawings
Specification includes a Sequence Listing.

(56) References Cited

FOREIGN PATENT DOCUMENTS

| WO | 2013/175658 A1 | 11/2013 |
|---|---|---|
| WO | 2013/178649 A1 | 12/2013 |
| WO | 2014/079773 A1 | 5/2014 |

OTHER PUBLICATIONS

De Freitas, J. R., et al., "Phosphate-solubilizing Rhizobacteria Enhance the Growth and Yield but not Phosphorus Uptake of Canola (Brassica napus L.)," Biology and Fertility of Soils, May 1997, pp. 358-364, vol. 24, Issue 4.

Lopez-Bucio, J., et al., "Bacillus megaterium Rhizobacteria Promote Growth and Alter Root-System Architecture Through an Auxin- and Ethylene-Independent Signaling Mechanism in Arabidopsis thaliana," Molecular Plant-Microbe Interactions, 2007, pp. 207-217, vol. 20, No. 2.

Raddadi, N., et al., "Screening of Plant Growth Promoting Traits of Bacillus thuringiensis," Annals of Microbiology, 2008, pp. 47-52, vol. 58, No. 1.

Selvakumar, G., et al., "Isolation and Characterization of Nonrhizobial Plant Growth Promoting Bacteria from Nodules of Kudzu (Pueraria thunbergiana) and Their Effect on Wheat Seedling Growth," Current Microbiology, Feb. 2008, pp. 134-139, vol. 56, Issue 2.

Anand, R., et al., "N2-Fixation and Seedling Growth Promotion of Lodgepole Pine by Endophytic Paenibacillus polymyxa," Microbial Ecology, 2013, pp. 369-374, vol. 66, No. 2.

Bent, E., et al., "Alterations in Plant Growth and in Root Hormone Levels of Lodgepole Pines Inoculated with Rhizobacteria," Canadian Journal of Microbiology, Sep. 2001, pp. 793-800, vol. 47, No. 9.

Chakraborty, U., et al., "Plant Growth Promotion and Induction of Resistance in Camellia sinensis by Bacillus megaterium," Journal of Basic Microbiology, 2006, pp. 186-195, vol. 46, No. 3.

Choudhary, D. K., et al., "Interactions of Bacillus spp. and Plants—With Special Reference to Induced Systemic Resistance (ISR)," Microbiological Research, 2009, pp. 493-513, vol. 164.

Da Mota, F. F., et al., "Auxin Production and Detection of the Gene Coding for the Auxin Efflux Carrier (AEC) Protein in Paenibacillus polymyxa," Journal of Microbiology, Jun. 2008, pp. 257-264, vol. 46, No. 3.

Ding, Y., et al., "Isolation and Identification of Nitrogen-Fixing Bacilli from Plant Rhizospheres in Beijing Region," Journal of Applied Microbiology, 2005, pp. 1271-1281, vol. 99, No. 5.

Doronina, N. V., et al., "Emended Description of Paracoccus kondratievae," International Journal of Systematic and Evolutionary Microbiology, Mar. 2002, pp. 679-682, vol. 52, Part 2.

English, M. M., et al., "Overexpression of has in the Plant Growth-Promoting Bacterium Enterobacter cloacae UW5 Increases Root Colonization," Journal of Applied Microbiology, 2009, pp. 2180-2190, vol. 108, No. 6.

Erturk, Y., et al., "Effects of Plant Growth Promoting Rhizobacteria (PGPR) on Rooting and Root Growth of Kiwifruit (Actinidia deliciosa) Stem Cuttings," Biological Research, 2010, pp. 91-98, vol. 43, No. 1.

Faria, D. C., et al., "Endophytic Bacteria Isolated From Orchid and Their Potential to Promote Plant Growth," World Journal of Microbiology & Biotechnology, 2013, pp. 217-221, vol. 29, No. 2.

Forage, R. G., et al., "Glycerol Fermentation in Klebsiella pneumoniae: Functions of the Coenzyme B12-Dependent Glycerol and Diol Dehydratases," Journal of Bacteriology, Feb. 1982, pp. 413-419, vol. 149, No. 2.

Haggag, W. M., et al., "Colonization of Peanut Roots by Biofilm-Forming Paenibacillus polymyxa Initiates Biocontrol Against Crown Rot Disease," Journal of Applied Microbiology, 2008, pp. 961-969, vol. 104, No. 4.

Hinion, D. M., et al., "Enterobacter cloacae is an Endophytic Symbiont of Corn," Mycopathologia, 1995, pp. 117-125, vol. 129, No. 2.

Hontzeas, N., et al., "Changes in Gene Expression in Canola Roots Induced by ACC-Deaminase-Containing Plant-Growth-Promoting Bacteria," Molecular Plant-Microbe Interactions, Aug. 2004, pp. 865-871, vol. 17, No. 8.

Iniguez, A. L., et al., "Nitrogen Fixation in Wheat Provided by Klebsiella pneumoniae 342," Molecular Plant-Microbe Interactions, Oct. 2004, pp. 1078-1085, vol. 17, No. 10.

International Search Report and Written Opinion issued for PCT/US2014/030726, dated Aug. 19, 2014, 13 pages.

Islam, M. R., et al., "Characterization of Plant Growth-Promoting Traits of Free-Living Diazotrophic Bacteria and Their Inoculation Effects on Growth and Nitrogen Uptake of Crop Plants," Journal of Microbiology and Biotechnology, Oct. 2009, pp. 1213-1222, vol. 19, No. 10.

Jeong, H., et al., "Draft Genome Sequence of the Paenibacillus polymyxa Type Strain (ATCC 8421), A Plant Growth-Promoting Bacterium," Journal of Bacteriology, 2011, pp. 5026-5027, vol. 193, No. 18.

Karakurt, H., et al., "Effects of Indol-3-butyric Acid (IBA), Plant Growth Promoting Rhizobacteria (PGPR) and Carbohydrates on Rooting of Hardwood Cutting of MM106 Apple Rootstock," African Journal of Agricultural Research, Feb. 2009, pp. 060-064, vol. 4, No. 2.

Khan, Z., et al., "A Plant Growth Promoting Rhizobacterium, Paenibacillus polymyxa Strain GBR-1, Suppresses Root-Knot Nematode," Bioresource Technology, May 2008, pp. 3016-3023, vol. 99, No. 8.

Kim, J. F., et al., "Genome Sequence of the Polymyxin-Producing Plant-Probiotic Rhizobacterium Paenibacillus polymyxa E681," Journal of Bacteriology, 2010, pp. 6103-6104, vol. 192, No. 22.

Kishore, G. K., et al., "Phylloplane Bacteria Increase Seedling Emergence, Growth and Yield of Field-Grown Groundnut (Arachis hypogaea L.)," Letters in Applied Microbiology, 2005, pp. 260-268, vol. 40, No. 4.

Lamsal, K., et al., "Application of Rhizobacteria for Plant Growth Promotion Effect and Biocontrol of Anthracnose Caused by Colletotrichum acutatum on Pepper," Mycobiology, Dec. 2012, pp. 244-251, vol. 40, No. 4.

Lee, S., et al., "Growth Promotion of Xanthium italicum by Application of Rhizobacterial Isolates of Bacillus aryabhattai in Microcosm Soil," Journal of Microbiology, Feb. 2012, pp. 45-49, vol. 50, No. 1.

Leite, H. A., et al., "Bacillus subtilis and Enterobacter cloacae Endophytes From Healthy Theobroma cacao L. Trees can Systemically Colonize Seedlings and Promote Growth," Applied Microbiology and Biotechnology, Dec. 2012, pp. 2639-2651, vol. 97, No. 6.

Leveau, J. H. J., et al., "Utilization of the Plant Hormone Indole-3-Acetic Acid for Growth by Pseudomonas putida Strain 1290," Applied and Environmental Microbiology, May 2005, pp. 2365-2371, vol. 71, No. 5.

Li, J. et al. "An ACC Deaminase Minus Mutant of Enterobacter cloacae UW4 No Longer Promotes Root Elongation," Current Microbiology, Aug. 2000, pp. 101-105, vol. 41, No. 2.

Liu, X., et al., "Colonization of Maize and Rice Plants by Strain Bacillus megaterium C4," Current Microbiology, 2006, pp. 186-190, vol. 52, No. 3.

Liu, Y., et al., "Study on Mechanisms of Colonization of Nitrogen-Fixing PGPB, Klebsiella pneumoniae NG14 on the Root Surface of Rice and the Formation of Biofilm," Current Microbiology, 2011, pp. 1113-1122, vol. 62, No. 4.

Lopez-Bucio, J., et al., "Bacillus megaterium Rhizobacteria Promote Growth and Alter Root-System Architecture Through an Auxin- and Ethylene-Independent Signaling Mechanism in Arabidopsis thaliana," Molecular Plant-Microbe Interactions, Feb. 2007, pp. 207-217, vol. 20, No. 2.

Madmony, A., et al., "Enterobacter cloacae, an Obligatory Endophyte of Pollen Grains of Mediterranean Pines," Folia Microbiologica (Praha), 2005, pp. 209-216, vol. 50, No. 3.

Maes, M., et al., "Experiences and Perspectives for the Use of a Paenibacillus Strain as a Plant Protectant," Communications in Agricultural and Applied Biological Sciences, 2003, pp. 457-462, vol. 68, No. 4, Part B.

(56) References Cited

OTHER PUBLICATIONS

Marulanda, A., et al., "Regulation of Plasma Membrane Aquaporins by Inoculation with a Bacillus megaterium Strain in Maize (*Zea mays* L.) Plants Under Unstressed and Salt-Stressed Conditions," Planta, 2010, pp. 533-543, vol. 232, No. 2.

Meldau, D. G., et al., "A Native Plant Growth Promoting Bacterium, *Bacillus* sp. B55, Rescues Growth Performance of an Ethylene-Insensitive Plant Genotype in Nature," Frontiers in Plant Science, Jun. 2012, pp. 1-13, vol. 3, Article 112.

Non-Final Office Action dated Aug. 27, 2015, for U.S. Appl. No. 14/213,238, 20 pages.

Ortiz-Castro, R., et al., "Plant Growth Promotion by Bacillus megaterium Involves Cytokinin Signaling," Plant Signaling & Behavior, Apr. 2008, pp. 263-265, vol. 3, No. 4.

Penrose, D. M., et al., "Levels of ACC and Related Compounds in Exudate and Extracts of Canola Seeds Treated with ACC Deaminase-Containing Plant Growth-Promoting Bacteria," Canadian Journal of Microbiology, Apr. 2001, pp. 368-372, vol. 47, No. 4.

Pereira, C. E., et al., "Compatibility Among Fungicide Treatments on Soybean Seeds Through Film Coating and Inoculation with Bradyrhizobium Strains," Acta Scientiarum. Agronomy, Oct./Dec. 2010, pp. 585-589, vol. 32, No. 4.

Petrov, K., et al., "High Production of 2,3-butanediol From Glycerol by Klebsiella pneumoniae G31," Applied Microbiology and Biotechnology, 2009, pp. 659-665, vol. 84, No. 4.

Phi, Q. T., et al., "Assessment of Root-Associated Paenibacillus polymyxa Groups on Growth Promotion and Induced Systemic Resistance in Pepper," Journal of Microbiology and Biotechnology, Dec. 2010, pp. 1605-1613, vol. 20, No. 12.

Prusty, R., et al., "The Plant Hormone Indoleacetic Acid Induces Invasive Growth in *Sacchharomyces cerevisiae*," Proceedings of the National Academy of Sciences of the United States of America, Mar. 23, 2004, pp. 4153-4157, vol. 101, No. 12.

Rajendran, G., et al., "Enhanced Growth and Nodulation of Pigeon Pea by Co-Inoculation of Bacillus Strains with *Rhizobium* spp," Bioresource Technology, 2007, pp. 4544-4550, vol. 99, No. 11.

Rajkumar, M., et al., "Effects of Inoculation of Plant-Growth Promoting Bacteria on Ni Uptake by Indian Mustard," Bioresource Technology, 2008, pp. 3491-3498, vol. 99, No. 9.

Response to Notice of Missing Parts and Preliminary Amendment A filed on Jun. 2, 2014, for U.S. Appl. No. 14/213,238, 12 pages.

Response to Restriction Requirement and Amendment B filed on May 12, 2015, for U.S. Appl. No. 14/213,238, 9 pages.

Response to Office Action and Amendment C filed on Nov. 24, 2015, for U.S. Appl. No. 14/213,238, 11 pages.

Restriction Requirement dated Mar. 12, 2015, for U.S. Appl. No. 14/213,238, 12 pages.

Ryu, C. M., et al., "Bacterial Volatiles Promote Growth in Arabidopsis," Proceedings of the National Academy of Sciences of the United States of America, Apr. 2003, pp. 4927-4932, vol. 100, No. 8.

Sachdev, D. P., et al., "Isolation and Characterization of Indole Acetic Acid (IAA) Producing Klebsiella pneumoniae Strains from Rhizosphere of Wheat (*Triticum aestivum*) and Their Effect on Plant Growth," Indian Journal of Experimental Biology, Dec. 2009, pp. 993-1000, vol. 47, No. 12.

Saleh, S. S., et al., "Involvement of gacS and rpoS in Enhancement of the Plant Growth-Promoting Capabilities of Enterobacter cloacae CAL2 and UW4," Canadian Journal of Microbiology, Aug. 2001, pp. 698-705, vol. 47, No. 8.

Shahid, M., et al., "Root Colonization and Growth Promotion of Sunflower (*Helianthus annuus* L.) by Phosphate Solubilizing Enterobacter sp. Fs-11," World Journal of Microbiology & Biotechnology, 2012, pp. 2749-2758, vol. 28, No. 8.

Shankar, M., et al., "Root Colonization of a Rice Growth Promoting Strain of Enterobacter cloacae," Journal of Basic Microbiology, 2011, pp. 523-530, vol. 51, No. 5.

Thomas, P., et al., "Endophytic Bacteria Associated with Growing Shoot Tips of Banana (*Musa* sp.) cv. Grand Naine and the Affinity of Endophytes to the Host," Microbial Ecology, 2009, pp. 952-964, vol. 58, No. 4.

Timmusk, S., et al., "The Plant-Growth-Promoting Rhizobacterium Paenibacillus polymyxa Induces Changes in *Arabidopsis thaliana* Gene Expression: A Possible Connection Between Biotic and Abiotic Stress Responses," Molecular Plant-Microbe Interactions, Nov. 1999, pp. 951-959, vol. 12, No. 11.

Timmusk, S., et al., "Paenibacillus polymyxa Invades Plant Roots and Forms Biofilms," Applied and Environmental Microbiology, Nov. 2005, pp. 7292-7300, vol. 71, No. 11.

Trivedi, P., et al., "Plant Growth Promotion Abilities and Formulation of Bacillus megaterium Strain B 388 (MTCC6521) Isolated From a Temperate Himalayan Location," Indian Journal of Microbiology, 2008, pp. 342-347, vol. 48, No. 3.

Vendan, R. T., et al., "Diversity of Endophytic Bacteria in Ginseng and Their Potential for Plant Growth Promotion," Journal of Microbiology, 2010, pp. 559-565, vol. 48, No. 5.

Von Der Weid, I., et al., "Diversity of Paenibacillus polymyxa Strains Isolated From the Rhizosphere of Maize Planted in Cerrado Soil," Research in Microbiology, Jun. 2000, pp. 369-381, vol. 151, No. 5.

Walker, R., et al., "Colonization of the Developing Rhizosphere of Sugar Beet Seedlings by Potential Biocontrol Agents Applied as Seed Treatments," Journal of Applied Microbiology, 2002, pp. 228-237, vol. 92, No. 2.

Yadav, S., et al., "Diversity and Phylogeny of Plant Growth-Promoting Bacilli from Moderately Acidic Soil," Journal of Basic Microbiology, Feb. 2011, pp. 98-106, vol. 51, No. 1.

Yegorenkova, I. V., et al., "Paenibacillus polymyxa Rhizobacteria and Their Synthesized Exoglycans in Interaction With Wheat Roots: Colonization and Root Hair Deformation," Current Microbiology, 2013, pp. 481-486, vol. 66, No. 5.

Ziegler, D. R., Bacillus Thuringiensis Bacillus Cereus, Bacillus Genetic Stock Center Catalog of Strains, 1999, Seventh Edition, vol. 2.

Zou, C., et al., "Bacillus megaterium Strain XTBG34 Promotes Plant Growth by Producing 2-pentylfuran," Journal of Microbiology, Aug. 2010, pp. 460-466, vol. 48, No. 4.

Goldberg, L. J., et al., "A Bacterial Spore Demonstrating Rapid Larvicidal Activity Against Anopheles sergentii, Uranotaenia unguiculata, Culex univitattus, Aedes aegypti and Culex pipiens," Mosquito News, Sep. 1977, pp. 355-358, vol. 37, No. 3.

Guerchicoff, A., et al., "Identification and Characterization of a Previously Undescribed cyt Gene in Bacillus thuringiensis subsp. israelensis," Applied and Environmental Microbiology, Jul. 1997, pp. 2716-2721, vol. 63, No. 7.

Diaz, K., et al., "Root-Promoting Rhizobacteria in Eucalyptus globulus Cuttings," World Journal of Microbiology and Biotechnology, 2009, pp. 867-873, vol. 25.

GenBank Accession No. JX047442.1, "*Bacillus* sp. SDT11 16S ribosomal RNA gene, Partial Sequence," accessed fom NCBI website at <http://www.ncbi.nlm.nih.gov/nuccore/JX047442.1> on Jul. 10, 2012, 1 page.

Siddikee, Md. A., et al., "Regulation of Ethylene Biosynthesis Under Salt Stress in Red Pepper (*Capsicum annuum* L.) by 1-Aminocyclopropane-1-Carboxylic Acid (ACC) Deaminase-Producing Halotolerant Bacteria," Journal of Plant Growth Regulation, 2012, pp. 265-272, vol. 31, Issue 2.

Wang, W., et al., "Comparative Proteomic Analysis of Rice Seedlings in Response to Inoculation with Bacillus cereus," Letters in Applied Microbiology, 2012, pp. 208-215, vol. 56, Issue 3.

Egorov, M. A., et al., "Growth Stimulating Effect of a Bacilus megaterium Strain in the Greenhouse Experiment," Vestnik of Altay State Agricultural University, 2012, pp. 46-49, vol. 89, No. 3.

Ahemad, M., et al., "Mechanisms and Applications of Plant Growth Promoting Rhizobacteria: Current Prespective," Journal of King Saud University—Science, 2014, pp. 1-20, vol. 26.

Li, L., et al., "Genetically Modified Bacillus thuringiensis Biopesticides," Bacillus thuringiensis Biotechnology, 2012, Chapter 13, pp. 231-232.

Lopez-Pazos, S. A., et al., "Presence and Significance of Bacillus thuringiensis Cry Proteins Associated with the Andean Weevil Premnotrypes vorax (Coleoptera: Curculionidae)," Revista de Biologia Tropical, Dec. 2009, pp. 1235-1243, vol. 57, No. 4.

(56) References Cited

OTHER PUBLICATIONS

Palkova, Z., "Multicellular Microorganisms: Laboratory Versus Nature," European Molecular Biology Organization Reports, 2004, pp. 470-476, vol. 5, No. 5.
Non-Final Office Action issued for U.S. Appl. No. 15/211,044 dated Dec. 5, 2018, 12 pages.

* cited by examiner

SEQUENCE LISTING

<160> NUMBER OF SEQ ID NOS: 21

<210> SEQ ID NO 1
<211> LENGTH: 717
<212> TYPE: DNA
<213> ORGANISM: Bacillus aryabhattai
<220> FEATURE:
<221> NAME/KEY: misc_feature
<222> LOCATION: (3)..(4)
<223> OTHER INFORMATION: n = a, c, g, or t

<400> SEQUENCE: 1

```
ggnncaacgc cgcgtgagtg atgaaggctt tcgggtcgta aaactctgtt gttagggaag      60
aacaagtacg agagtaactg ctcgtacctt gacggtacct aaccagaaag ccacggctaa     120
ctacgtgcca gcagccgcgg taatacgtag gtggcaagcg ttatccggaa ttattgggcg     180
taaagcgcgc gcaggcggtt tcttaagtct gatgtgaaag cccacggctc aaccgtggag     240
ggtcattgga aactgggaa cttgagtgca gaagagaaaa gcggaattcc acgtgtagcg     300
gtgaaatgcg tagagatgtg gaggaacacc agtggcgaag gcggcttttt ggtctgtaac     360
tgacgctgag gcgcgaaagc gtggggagca aacaggatta gataccctgg tagtccacgc     420
cgtaaacgat gagtgctaag tgttagaggg tttccgccct ttagtgctgc agctaacgca     480
ttaagcactc cgcctgggga gtacggtcgc aagactgaaa ctcaaaggaa ttgacggggg     540
cccgcacaag cggtggagca tgtggtttaa ttcgaagcaa cgcgaagaac cttaccaggt     600
cttgacatcc tctgacaact ctagatag agcgttcccc ttcgggggac agagtgacag     660
gtggtgcatg gttgtcgtca gctcgtgtcg tgagatgttg ggttaagtcc cgcaacg         717
```

```
<210> SEQ ID NO 2
<211> LENGTH: 718
<212> TYPE: DNA
<213> ORGANISM: Bacillus aryabhattai
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (9)..(10)
<223> OTHER INFORMATION: n = a, c, g, or t

<400> SEQUENCE: 2
tctganggnn cacgccgcgt gagtgatgaa ggctttcggg tcgtaaaact ctgttgttag      60
ggaagaacaa gtacgagagt aactgctcgt accttgacgg tacctaacca gaaagccacg     120
gctaactacg tgccagcagc cgcggtaata cgtaggtggc aagcgttatc cggaattatt     180
gggcgtaaag cgcgcgcagg cggtttctta agtctgatgt gaaagcccac ggctcaaccg     240
tggagggtca ttggaaactg ggaacttga gtgcagaaga gaaaagcgga attccacgtg      300
tagcggtgaa atgcgtagag atgtggagga acaccagtgg cgaaggcggc ttttggtct     360 gtaactgacg ctgaggcgcg aaagcgtggg gagcaaacag gattagatac cctggtagtc     420
cacgccgtaa acgatgagtg ctaagtgtta gagggtttcc gccctttagt gctgcagcta     480
acgcattaag cactccgcct ggggagtacg gtcgcaagac tgaaactcaa aggaattgac     540
gggggcccgc acaagcggtg gagcatgtgg tttaattcga agcaacgcga agaaccttac     600
caggtcttga catcctctga caactctaga gatagagcgt tccccttcgg gggacagagt    660
gacaggtggt gcatggttgt cgtcagctcg tgtcgtgaga tgttgggtta agtcccgc      718

<210> SEQ ID NO 3
<211> LENGTH: 716
<212> TYPE: DNA
<213> ORGANISM: Bacillus flexus
<220> FEATURE:
<221> NAME/KEY: misc_feature
<222> LOCATION: (4)..(4)
<223> OTHER INFORMATION: n = a, c, g, or t
<220> FEATURE:
<221> NAME/KEY: misc_feature
<222> LOCATION: (22)..(22)
<223> OTHER INFORMATION: n = a, c, g, or t

<400> SEQUENCE: 3
ggancaacgc cgcgtgagtg angaaggctt tcgggtcgta aaactctgtt gttagggaag      60
aacaagtaca agagtaactg cttgtacctt gacggtacct aaccagaaag ccacggctaa    120
ctacgtgcca gcagccgcgg taatacgtag gtggcaagcg ttatccggaa ttattgggcg    180
taaagcgcgc gcaggcggtt tcttaagtct gatgtgaaag cccacggctc aaccgtggag    240
ggtcattgga aactgggaa cttgagtgca agagagaaaa gcggaattcc acgtgtagcg    300
gtgaaatgcg tagagatgtg gaggaacacc agtggcgaag gcggcttttt ggtctgtaac    360
tgacgctgag gcgcgaaagc gtggggagca acaggattaa gataccctgg tagtccacgc    420
cgtaaacgat gagtgctaag tgttagaggg tttccgccct ttagtgctgc agctaacgca    480
ttaagcactc cgcctgggga gtacggtcgc aagactgaaa ctcaaaggaa ttgacggggg    540
cccgcacaag cggtggagca tgtggtttaa ttcgaagcaa cgcgaagaac cttaccaggt    600
cttgacatcc tctgacaact ctagagatag agcgttcccc ttcggggac agagtgacag    660
```

```
gtggtgcatg gttgtcgtca gctcgtgtcg tgagatgttg ggttaagtcc cgcaac        716
```

```
<210> SEQ ID NO 4
<211> LENGTH: 676
<212> TYPE: DNA
<213> ORGANISM: Paracoccus kondratievae
<220> FEATURE:
<221> NAME/KEY: misc_feature
<222> LOCATION: (13)..(15)
<223> OTHER INFORMATION: n = a, c, g, or t
<220> FEATURE:
<221> NAME/KEY: misc_feature
<222> LOCATION: (19)..(19)
<223> OTHER INFORMATION: n = a, c, g, or t
<220> FEATURE:
<221> NAME/KEY: misc_feature
<222> LOCATION: (44)..(44)
<223> OTHER INFORMATION: n = a, c, g, or t

<400> SEQUENCE: 4
gccgcgtgag tgnnnaagnc cctagggttg taaagctctt tcanctggga agataatgac     60
tgtaccagca gaagaagccc cggctaactc cgtgccagca gccgcggtaa tacgagggg     120 gctagcgttg ttcggaatta ctgggcgtaa agcgcacgta ggcggaccgg aaagttgggg    180
gtgaaatccc ggggctcaac cccggaactg ccttcaaaac tatcggtctg gagttcgaga    240
gaggtgagtg gaattccgag tgtagaggtg aaattcgtag atattcggag gaacaccagt    300
ggcgaaggcg gctcactggc tcgatactga cgctgaggtg cgaaagcgtg gggagcaaac    360
aggattagat accctggtag tccacgccgt aaacgatgaa tgccagtcgt cgggcagcat    420
gctgttcggt gacacaccta acggattaag cattccgcct ggggagtacg gtcgcaagat    480
taaaactcaa aggaattgac ggggccccgc acaagcggtg gagcatgtgg tttaattcga    540
agcaacgcgc agaaccttac caaccccttga catcccagga cagcccgaga gatcgggtct    600
ccacttcggt ggcctggaga caggtgctgc atggctgtcg tcagctcgtg tcgtgagatg    660
ttcggttaag tccggc                                                    676
```

```
<210> SEQ ID NO 5
<211> LENGTH: 728
<212> TYPE: DNA
<213> ORGANISM: Enterobacter cloacae
<220> FEATURE:
<221> NAME/KEY: misc_feature
<222> LOCATION: (4)..(5)
<223> OTHER INFORMATION: n = a, c, g, or t
<220> FEATURE:
<221> NAME/KEY: misc_feature
<222> LOCATION: (12)..(12)
<223> OTHER INFORMATION: n = a, c, g, or t
<220> FEATURE:
<221> NAME/KEY: misc_feature
<222> LOCATION: (33)..(33)
<223> OTHER INFORMATION: n = a, c, g, or t
<220> FEATURE:
<221> NAME/KEY: misc_feature
<222> LOCATION: (719)..(719)
<223> OTHER INFORMATION: n = a, c, g, or t
<220> FEATURE:
<221> NAME/KEY: misc_feature
<222> LOCATION: (721)..(722)
<223> OTHER INFORMATION: n = a, c, g, or t

<400> SEQUENCE: 5
ctgnngcagc cntgccgcgt gtatgaagaa ggncttcggg ttgtaaagta ctttcagcgg     60
ggaggaaggt gttgtggtta ataaccacag caattgacgt tacccgcaga agaagcaccg    120
gctaactccg tgccagcagc cgcggtaata cggagggtgc aagcgttaat cggaattact    180
```

```
gggcgtaaag cgcacgcagg cggtctgtca agtcggatgt gaaatccccg ggctcaacct    240
gggaactgca ttcgaaactg gcaggctaga gtcttgtaga gggggggtaga attccaggtg    300 tagcggtgaa atgcgtagag atctggagga ataccggtgg cgaaggcggc ccctggaca     360 aagactgacg ctcaggtgcg aaagcgtggg gagcaaacag gattagatac cctggtagtc    420
cacgccgtaa acgatgtcga tttggaggtt gtgcccttga ggcgtggctt ccggagctaa    480
cgcgttaaat cgaccgcctg ggagtacggc cgcaaggtt aaaactcaaa tgaattgacg    540
ggggcccgca caagcggtgg agcatgtggt ttaattcgat gcaacgcgaa gaaccttacc    600
tggtcttgac atccacagaa ctttccagag atggattggg gccttcggga actgtgagac    660
aggtgctgca tggctgtcgt cagctcgtgt tgtgaaatgt tgggttaagt cccgcaacna   720 nncgcaac                                                           728
```

```
<210> SEQ ID NO 6
<211> LENGTH: 717
<212> TYPE: DNA
<213> ORGANISM: Bacillus nealsonii
<220> FEATURE:
<221> NAME/KEY: misc_feature
<222> LOCATION: (3)..(4)
<223> OTHER INFORMATION: n = a, c, g, or t
<220> FEATURE:
<221> NAME/KEY: misc_feature
<222> LOCATION: (8)..(8)
<223> OTHER INFORMATION: n = a, c, g, or t

<400> SEQUENCE: 6
```

```
tgnnggnaca acgccgcgtg agtgatgaag gttttcggat cgtaaaactc tgttgttagg     60
gaagaacaag tacgagagta actgctcgta ccttgacggt acctaaccag aaagccacgg    120
ctaactacgt gccagcagcc gcggtaatac gtaggtggca agcgttgtcc ggaattattg    180
ggcgtaaagc gcgcgcaggc ggtcctttaa gtctgatgtg aaagcccacg gctcaaccgt    240
ggagggtcat tggaaactgg gggacttgag tgcagaagag aagagtggaa ttccacgtgt    300
agcggtgaaa tgcgtagaga tgtggaggaa caccagtggc gaaggcgact ctttggtctg    360
taactgacgc tgaggcgcga aagcgtgggg agcaaacagg attagatacc ctggtagtcc    420
acgccgtaaa cgatgagtgc taagtgttag agggtttccg cccttagtg ctgcagcaaa    480 cgcattaagc actccgcctg ggagtacggc cgcaaggct gaaactcaaa ggaattgacg    540
ggggcccgca caagcggtgg agcatgtggt ttaattcgaa gcaacgcgaa gaaccttacc    600
aggtcttgac atcctctgac aatcctagag ataggacgtt ccccttcggg ggacaggatg    660
acaggtggtg catggttgtc gtcagctcgt gtcgtgagat gttgggttaa gtcccgc       717
```

```
<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
actcctacgg gaggcagcag t                                               21
```

```
<210> SEQ ID NO 8
<211> LENGTH: 16
<212> TYPE: DNA
<213> ORGANISM: Artificial sequence
<220> FEATURE:
```

<223> OTHER INFORMATION: Primter

<400> SEQUENCE: 8
gggttgcgct cgttgc                                                    16

<210> SEQ ID NO 9
<211> LENGTH: 16
<212> TYPE: DNA
<213> ORGANISM: Artificial sequence
<220> FEATURE:
<223> OTHER INFORMATION: Primer

<400> SEQUENCE: 9
gggttgcgct cgttac                                                    16

<210> SEQ ID NO 10
<211> LENGTH: 711
<212> TYPE: DNA
<213> ORGANISM: Bacillus mycoides
<220> FEATURE:
<221> NAME/KEY: misc_feature
<222> LOCATION: (20)..(21)
<223> OTHER INFORMATION: n is a, c, g, or t

<400> SEQUENCE: 10
ggagcacgcc gcgtgagtgn ngaaggcttt cgggtcgtaa aactctgttg ttagggaaga     60
acaagtgcta gttgaataag ctggcacctt gacggtacct aaccagaaag ccacggctaa    120
ctacgtgcca gcagccgcgg taatacgtag gtggcaagcg ttatccggaa ttattgggcg    180
taaagcgcgc gcaggtggtt tcttaagtct gatgtgaaag cccacggctc aaccgtggag    240
ggtcattgga aactgggaga cttgagtgca gaagaggaaa gtggaattcc atgtgtagcg    300
gtgaaatgcg tagagatatg gaggaacacc agtggcgaag cgactttctg gtctgtaac    360 tgacactgag gcgcgaaagc gtgggagca acaggatta gatacctgg tagtccacgc     420 cgtaaacgat gagtgctaag tgttagaggg tttcgcccct ttagtgctga agttaacgca    480
ttaagcactc cgcctgggga gtacggccgc aaggctgaaa ctcaaaggaa ttgacggggg    540
cccgcacaag cggtggagca gtggttttaa ttcgaagcaa cgcgaagaac cttaccaggt    600
cttgacatcc tctgaaaact ctagagatag agcttctcct tcgggagcag agtgacaggt    660
ggtgcatggt tgtcgtcagc tcgtgtcgtg agatgttggg ttaagtcccg c             711

<210> SEQ ID NO 11
<211> LENGTH: 702
<212> TYPE: DNA
<213> ORGANISM: Bacillus subtilis

<400> SEQUENCE: 11
cgccgcgtga gtgatgaagg ttttcggatc gtaaagctct gttgttaggg aagaacaagt     60
gccgttcaaa tagggcggca ccttgacggt acctaaccag aaagccacgg ctaactacgt    120
gccagcagcc gcggtaatac gtaggtggca agcgttgtcc ggaattattg ggcgtaaagg    180
gctcgcaggc ggtttcttaa gtctgatgtg aaagcccccg gctcaaccgg ggagggtcat    240
tggaaactgg ggaacttgag tgcagaagag gagagtggaa ttccacgtgt agcggtgaaa    300
tgcgtagaga tgtggaggaa caccagtggc gaaggcgact ctctggtctg taactgacgc    360
tgaggagcga aagcgtgggg agcgaacagg attagatacc ctggtagtcc acgccgtaaa    420
cgatgagtgc taagtgttag ggggtttccg ccccttagtg ctgcagctaa cgcattaagc    480
actccgcctg gggagtacgg tcgcaagact gaaactcaaa ggaattgacg ggccccgca    540

```
caagcggtgg agcatgtggt ttaattcgaa gcaacgcgaa gaaccttacc aggtcttgac    600
atcctctgac aatcctagag ataggacgtc cccttcgggg gcagagtgac aggtggtgca    660
tggttgtcgt cagctcgtgt cgtgagatgt tgggttaagt cc                       702
```

<210> SEQ ID NO 12
<211> LENGTH: 680
<212> TYPE: DNA
<213> ORGANISM: Alcaligenes faecalis
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (272)..(273)
<223> OTHER INFORMATION: n is a, c, g, or t

<400> SEQUENCE: 12

```
cttcggggttg taaagtactt ttggcagaga agaaaaggta tctcctaata cgagatactg    60
ctgacggtat ctgcagaata agcaccggct aactacgtgc cancagccgc ggtaatacgt    120
agggtgcaag cgttaatcgg aattactggg cgtaaagcgt gtgtaggcgg ttcggaaaga    180
aagatgtgaa atcccagggc tcaaccttgg aactgcattt ttaactgccg agctagagta    240
tgtcagaggg gggtagaatt cnnntgtagc anngaaatgc gtagatatgt ggaggaatac    300
cgatggcgaa ggcagccccc tgggataata ctgacgctca gacacgaaag cgtggggagc    360
aaacaggatt agataccctg gtagtccacg ccctaaacga tgtcaactag ctgttgggc    420 cgttaggcct tagtagcgca gctaacgcgt gaagttgacc gcctgggag tacggtcgca    480 agattaaaac tcaaaggaat tgacggggac ccgcacaagc ggtggatgat gtggattaat    540
tcgatgcaac gcgaaaaacc ttacctaccc ttgacatgtc tggaaagccg aagagatttg    600
gccgtgctcg caagagaacc ggaacacagg tgctgcatgg ctgtcgtcag ctcgtgtcgt    660
gagatgttgg gttaagtccc                                                680
```

<210> SEQ ID NO 13
<211> LENGTH: 719
<212> TYPE: DNA
<213> ORGANISM: Bacillus mycoides
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (640)..(642)
<223> OTHER INFORMATION: n is a, c, g, or t

<400> SEQUENCE: 13

```
aaagtctgac ggagcacgcc gcgtgagtga tgaaggcttt cgggtcgtaa aactctgttg    60
ttagggaaga acaagtgcta gttgaataag ctggcacctt gacggtacct aaccagaaag    120
ccacggctaa ctacgtgcca gcagccgcgg taatacgtag gtggcaagcg ttatccggaa    180
ttattgggcg taaagcgcgc gcaggtggtt tcttaagtct gatgtgaaag cccacggctc    240
aaccgtggag ggtcattgga aactgggaga cttgagtgca gaagaggaaa gtggaattcc    300
atgtgtagcg gtgaaatgcg tagagatatg gaggaacacc agtggcgaag gcgactttct    360
```

```
ggtctgtaac tgacactgag gcgcgaaagc gtggggagca aacaggatta gataccctgg    420
tagtccacgc cgtaaacgat gagtgctaag tgttagaggg tttccgccct ttagtgctga    480
agttaacgca ttaagcactc cgcctgggga gtacggccgc aaggctgaaa ctcaaaggaa    540
ttgacggggg cccgcacaag cggtggagca tgtggtttaa ttcgaagcaa cgcgaagaac    600
cttaccaggt cttgacatcc tctgaaaacn ctagagatan nncttctcct tcgggagcag    660
agtgacaggt ggtgcatggt tgtcgtcagc tcgtgtcgtg agatgttggg ttaagtccc     719
```

<210> SEQ ID NO 14
<211> LENGTH: 709
<212> TYPE: DNA
<213> ORGANISM: Bacillus mycoides

<400> SEQUENCE: 14

```
ggagcacgcc gcgtgagtga tgaaggcttt cgggtcgtaa aactctgttg ttagggaaga    60
acaagtgcta gttgaataag ctggcacctt gacggtacct aaccagaaag ccacggctaa    120
ctacgtgcca gcagccgcgg taatacgtag gtggcaagcg ttatccggaa ttattgggcg    180
taaagcgcgc gcaggtggtt tcttaagtct gatgtgaaag cccacggctc aaccgtggag    240
ggtcattgga aactgggaga cttgagtgca gaagaggaaa gtggaattcc atgtgtagcg    300
gtgaaatgcg tagagatatg gaggaacacc agtggcgaag gcgactttct ggtctgtaac    360
tgacactgag gcgcgaaagc gtggggagca aacaggatta gataccctgg tagtccacgc    420
cgtaaacgat gagtgctaag tgttagaggg tttccgccct ttagtgctga agttaacgca    480
ttaagcactc cgcctgggga gtacggccgc aaggctgaaa ctcaaaggaa ttgacggggg    540
cccgcacaag cggtggagca tgtggtttaa ttcgaagcaa cgcgaagaac cttaccaggt    600
cttgacatcc tctgacaacc ctagagatag gcttcccct tcgggggcag agtgacaggt    660
ggtgcatggt tgtcgtcagc tcgtgtcgtg agatgttggg ttaagtccc                709
```

<210> SEQ ID NO 15
<211> LENGTH: 713
<212> TYPE: DNA
<213> ORGANISM: Bacillus sp.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t

<400> SEQUENCE: 15

```
ggancaacgc cgcgtgagtg angaaggctt tcgggtcgta aaactctgtt gttagggaag    60
aacaagtgct agttgaataa gctggcacct tgacggtacc taaccagaaa gccacggcta    120
actacgtgcc agcagccgcg gtaatacgta ggtggcaagc gttatccgga attattgggc    180
gtaaagcgcg cgcaggtggt ttcttaagtc tgatgtgaaa gcccacggct caaccgtgga    240
gggtcattgg aaactgggag acttgagtgc agaagaggaa agtggaattc catgtgtagc    300
ggtgaaatgc gtagagatat ggaggaacac cagtggcgaa ggcgactttc tggtctgtaa    360
ctgacactga ggcgcgaaag cgtggggagc aaacaggatt agataccctg gtagtccacg    420
ccgtaaacga tgagtgctaa gtgttagagg gtttccgccc tttagtgctg aagttaacgc    480
```

```
attaagcact ccgcctgggg agtacggccg caaggctgaa actcaaagga attgacgggg      540
gcccgcacaa gcggtggagc atgtggttta attcgaagca acgcgaagaa ccttaccagg      600
tcttgacatc ctctgaaaac tctagagata gagcttctcc ttcgggagca gagtgacagg      660
tggtgcatgg ttgtcgtcag ctcgtgtcgt gagatgntgg gttaagtccc gca             713
```

<210> SEQ ID NO 16
<211> LENGTH: 876
<212> TYPE: DNA
<213> ORGANISM: Bacillus thuringiensis

<400> SEQUENCE: 16

```
tctgacgg

```
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (189)..(190)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
```

<222> LOCATION: (259)..(259)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (364)..(365)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (417)..(418)
<223> OTHER INFORMATION: n is a, c, g, or t
<220> FEATURE:

```
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (471)..(472)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (492)..(496)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (516)..(517)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
```

```
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (637)..(640)
<223> OTHER INFORMATION: n is a, c, g, or t

<400> SEQUENCE: 17
```

```
cttanngnnt gannnnnctt gnnaanaaag ccccggctaa ctacntgcca ncanccgcgg      60
taatacntan gngcaagcg ttgtccggaa ttattgggcg taaagcgcgc gcaggcggtc      120
ntttaagtct ggtgtttaag cccggggctc aaccccggat cncncgggaa actggatgac    180
ttgantgcnn aanaagagag tggaattccn ngtgtancgg tgaaatgcnt ananatgtgn    240
angaacacca ntggcnaang cnactctctg ggctgtaact gacnctgang cncgaaagcg    300
tggggagcaa acangattan ataccctggt antccacgcc ntanacnatn antgctaggt    360
gttnngggtt tcnataccct tgntgccnaa nttaacacat taancactcc gcctggnnan    420
tacngtcnca anantgaaac tcnnangaan tgacngggac ccgcacaagc nntgnantat    480
gtggtttaan tnnnnncaac ncnaanaanc ttaccnngnc ttgacatctn aatgaccngn    540
gcananatgt nccttccctt cngnacattc nngacaggtg gtgcatggnt gtcntcnnct    600
cntgtcnngn gatgttgggt taantccccg cancnannnn                         640

<210> SEQ ID NO 18
<211> LENGTH: 686
<212> TYPE: DNA
<213> ORGANISM: Bacillus sp.

<400> SEQUENCE: 18
aaggctttcg ggtcgtaaaa ctctgttgtt agggaagaac aagtgctagt tgaataagct    60
ggcaccttga cggtacctaa ccagaaagcc acggctaact acgtgccagc agccgcggta   120
atacgtaggt ggcaagcgtt atccggaatt attgggcgta aagcgcgcgc aggtggtttc   180
ttaagtctga tgtgaaagcc cacggctcaa ccgtgggg tcattggaaa ctggagact    240 tgagtgcaga agaggaaagt ggaattccat gtgtagcggt gaaatgcgta gagatatgga   300
ggaacaccag tggcgaaggc gactttctgg tctgtaactg acactgaggc gcgaaagcgt   360
ggggagcaaa caggattaga taccctggta gtccacgccg taaacgatga gtgctaagtg   420
ttagagggtt tccgcccttt agtgctgaag ttaacgcatt aagcactccg cctggggagt   480
acggccgcaa ggctgaaact caaaggaatt gacggggggcc cgcacaagcg gtggagcatg   540
tggtttaatt cgaagcaacg cgaagaacct taccaggtct tgacatcctc tgaaaaccct   600
agagataggg cttctccttc gggagcagag tgacaggtgg tgcatggttg tcgtcagctc   660
gtgtcgtgag atgttgggtt aagtcc                                        686

<210> SEQ ID NO 19
<211> LENGTH: 678
<212> TYPE: DNA
<213> ORGANISM: Bacillus subtilis
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t

<400> SEQUENCE: 19
aagctctgtt gttagggaag aacaagtacc gttcgaatag ggcggtacct tgacggtacc    60
```

```
taaccagaaa gccacggcta actacgtgcc agcagccgcg gtaatacgta ggtggcaagc      120
gttgtccgga attattgggc gtaaagggct cgcaggcggt ttcttaagtc tgatgtgaaa      180
gcccccggct caaccgggga gggtcattgg aaactgggga acttgagtgc agaagaggag      240
agtggaattc cacgtgtagc ggtgaaatgc gtagagatgt ggaggaacac cagtggcgaa      300
ggcgactctc tggtctgtaa ctgacgctga ggagcgaaag cgtggggagc gaacaggatt      360
agataccctg gtagtccacg ccgtaaacga tgagtgctaa gtgttagggg gtttccgccc      420
cttantgctg cagctaacgc attaagcact ccgcctgggg agtacggtcg caagactgaa      480
actcaaagga attgacgggg gcccgcacaa gcggtggagc atgtggttta attcgaagca      540
acgcgaanaa ccttaccagg tcttgacatc ctctgacaat cctagagata ggacgtcccc      600
ttcgggggca gagtgacagg tggtgcatgg ttgtcgtcan ctcgtgtcgt gagatgttgg      660
nttaagtccc gcaacgag                                                   678

<210> SEQ ID NO 20
<211> LENGTH: 743
<212> TYPE: DNA
<213> ORGANISM: Bacillus megaterium
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (689)..(691)
<223> OTHER INFORMATION: n is a, c, g, or t
<220> FEATURE:
<221> NAME/KEY: misc_feature
<222> LOCATION: (693)..(708)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (716)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t
<220> FEATURE:
<221> NAME/KEY: misc_feature
<222> LOCATION: (740)..(741)
<223> OTHER INFORMATION: n is a, c, g, or t

<400> SEQUENCE: 20 aagncttteg gnncgtaaaa ctctgttgtt agggaagaac aagtacgaga gtaactgctc       60
gtaccttgac ggtacctaac cagaaagcca cggctaacta cgtgccagca gccgcggtaa      120
```

```
tacgtaggtg gcaagcgtta tccggaatta ttgggcgtaa agcgcgcgca ggcggtttct    180
taagtctgat gtgaaagccc acggctcaac cgtggagggt cattggaaac tgggaactt     240 gagtgcagaa gagaaaagcg gaattccacg tgtagcggtg aaatgcgtag agatgtggag    300
gaacaccagt ggcgaaggcg gcttttctgt ctgtaactga cgctgaggcg cgaaagcgtg    360
gggagcaaac aggattagat accctggtag tccacgccgt aaacgatgag tgctaagtgt    420
tagagggttt ccgcccttta gtgctgcagc taacgcatta agcactccgc ctggggagta    480
cggtcgcaag actgaaactc aaaggaattg acggggcccc gcacaagcgg tggagcatgt    540
ggtttaattc gaagcaacgc gaagaacctt accaggtctt gacatcctct gacaactcta    600
gagatagagc gttccccttc ggggacaga gtgacaggtg gtgcatggtt gtcgtcagct     660
cgtgtcgtga gatgttgggt taagtcccnn ncnnnnnnnn nnnnnnnntc tnagannccgn    720 gctgacnann ccangcaccn ngg                                             743

<210> SEQ ID NO 21
<211> LENGTH: 717
<212> TYPE: DNA
<213> ORGANISM: Bacillus mycoides
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 21
gtctgangga ncacgccgcg tgagtgatga aggctttcgg gtcgtaaaac tctgttgtta    60
gggaagaaca agtgctagtt gaataagctg gcaccttgac ggtacctaac cagaaagcca   120
cggctaacta cgtgccagca gccgcggtaa tacgtaggtg gcaagcgtta tccggaatta   180
ttgggcgtaa agcgcgcgca ggtggttct taagtctgat gtgaaagccc acggctcaac    240
cgtggagggt cattggaaac tgggagactt gagtgcagaa gaggaaagtg gaattccatg   300
tgtagcggtg aaatgcgtag agatatggag gaacaccagt ggcgaaggcg actttctggt   360
ctgtaactga cactgaggcg cgaaagcgtg gggagcaaac aggattagat accctggtag   420
tccacgccgt aaacgatgag tgctaagtgt tagagggttt ccgcccttta gtgctgaagt    480
taacgcatta agcactccgc ctggggagta cggccgcaag gctgaaactc aaaggaattg   540
acggggcccc gcacaagcgg tggagcatgt ggtttaattc gaagcaacgc gaagaacctt   600
accaggtctt gacatcctct gacaacccta gagatagggc ttccccttcg ggggcagagt   660
gacaggtggt gcatggttgt cgtcagctcg tgtcgtgaga tgttgggtta agtcccg      717
```

PLANT GROWTH-PROMOTING BACTERIA AND METHODS OF USE

CROSS-REFERENCES TO RELATED APPLICATIONS

This application claims the benefit of U.S. Provisional Patent Application Ser. No. 61/790,476, filed Mar. 15, 2013, the entirety of which is herein incorporated by reference.

FIELD OF THE INVENTION

The present invention generally relates to bacteriologically pure bacterial cultures of novel strains of plant growth-promoting bacteria, and inoculums comprising the same. The invention is also directed to plant seeds coated with the inoculums, kits comprising the inoculums and methods for stimulating plant growth by using the claimed bacterial cultures and/or inoculums.

BACKGROUND OF THE INVENTION

Plant growth-promoting bacteria (PGPB) are associated with many, if not all, plant species and are commonly present in many environments. The most widely studied group of PGPB is plant growth-promoting rhizobacteria (PGPR), which colonize the root surfaces and the closely adhering soil interface, the rhizosphere. Inside the rhizosphere is a zone where bacteria, fungi, and other organisms compete for nutrients and for binding to the root structures of the plant. Both detrimental and beneficial bacteria can occupy the plant's roots. The presence of plant growth-promoting bacteria (PGPB) within or near the roots or seeds can lead to a healthier rhizosphere environment and healthier plants. These free living bacteria promote plant growth in agricultural crops and lead to increased growth and yield at harvest. The bacteria that colonize the roots and maintain their benefits throughout the growth cycle of the plant are especially desired for application during early growth or as a seed coating agent to agricultural crops.

The mechanisms that PGPBs use in promoting plant growth are diverse and often plant- or cultivar-specific. Several PGPB growth-promoting mechanisms are known, which can influence the plant in a direct or indirect manner. The direct mechanism involves increasing plant growth by supplying the plant with nutrients and hormones, such as by fixing nitrogen that is available to plants, synthesizing phytohormones, and providing nutrients such as phosphate to the plant. The indirect mechanism of action for PGPB occurs through the ability to control detrimental fungal and bacterial pathogens from establishing or surviving within the rhizosphere. This is usually achieved through the beneficial secretion of antifungals and other antibiotics by the PGPB. As an additional advantage, PGPBs can also lead to extensive remodeling of the plant root systems.

In recent years, a significant effort has been expanded to identify novel strains of plant growth-promoting bacteria, and use them to promote plant growth, thereby increasing the yield of plant product, reducing the use and amounts of fertilizers and herbicides, and providing other benefits for agricultural and horticultural communities.

SUMMARY OF THE INVENTION

In one aspect, the present invention is directed to a biologically pure bacterial culture wherein the bacteria in the bacterial culture is: (a) *Bacillus aryabhattai* strain CAP53 (NRRL No. B-50819); (b) *Bacillus aryabhattai* strain CAP56 (NRRL No. B-50817); (c) *Bacillus flexus* strain BT054 (NRRL No. B-50816); (d) *Paracoccus kondratievae* strain NC35 (NRRL No. B-50820); (e) *Bacillus mycoides* strain BT155 (NRRL No. B-50921); (f) *Enterobacter cloacae* strain CAP12 (NRRL No. B-50822); (g) *Bacillus nealsonii* strain BOBA57 (NRRL No. B-50821); (h) *Bacillus mycoides* strain EE118 (NRRL No. B-50918); (i) *Bacillus subtilis* strain EE148 (NRRL No. B-50927); (j) *Alcaligenes faecalis* strain EE107 (NRRL No. B-50920); (k) *Bacillus mycoides* strain EE141 (NRRL No. B-50916); (l) *Bacillus mycoides* strain BT46-3 (NRRL No. B-50922); (m) *Bacillus cereus* family member strain EE128 (NRRL No. B-50917); (n) *Bacillus thuringiensis* strain BT013A (NRRL No. B-50924); (o) *Paenibacillus massiliensis* strain BT23 (NRRL No. B-50923); (p) *Bacillus cereus* family member strain EE349 (NRRL No. B-50928); (q) *Bacillus subtilis* strain EE218 (NRRL No. B-50926); (r) *Bacillus megaterium* strain EE281 (NRRL No. B-50925); (s) salt-tolerant and thiram-resistant *Paracoccus* sp. NC35; (t) salt-tolerant and thiram-resistant *Bacillus mycoides* strain BT155; (u) thiram-resistant *Bacillus aryabhattai* CAP53; (v) thiram-resistant *Bacillus thuringiensis* BT013A; or (w) glyphosate-tolerant *Bacillus aryabhattai* CAP53.

Also provided are biologically pure bacterial cultures wherein bacteria in the bacterial cultures are mutants of any of the foregoing strains comprising one or more mutations which retain the ability to promote plant growth.

The present invention is also directed to an inoculum for application to plants, plant seeds, or a plant growth medium, wherein the inoculum comprises an effective amount of a biologically pure bacterial culture disclosed herein and an agriculturally acceptable carrier.

Yet another aspect of the present invention is a method for stimulating plant growth by applying the biologically pure bacterial culture or the inoculum as disclosed herein to a plant, plant seed, or plant growth medium.

The present invention also provides a method for stimulating plant growth by applying glycerol, pyruvate, yeast extract, a polyol (e.g., mannitol, sorbitol, galactitol, fucitol, iditol, inositol, arabitol, xylitol, ribitol), polyethylene glycol, or a combination thereof to a plant growth medium, and applying at least one bacterial culture or at least one inoculum to a plant or plant seed in the plant growth medium, or to the plant growth medium, wherein the at least one bacterial culture or at least one inoculum is capable of stimulating plant growth.

Another aspect of the present invention is a provision of a plant seed coated with the inoculum or with the bacterial culture disclosed herein.

Yet another aspect of the present invention is a kit for stimulating plant growth comprising an inoculum disclosed herein and instructions for applying the inoculum to plants, plant seeds, or a plant growth medium.

Other objects and features will be in part apparent and in part pointed out hereinafter.

DEFINITIONS

A "biologically pure bacterial culture" refers to a culture of bacteria containing no other bacterial species in quantities sufficient to interfere with the replication of the culture or be detected by normal bacteriological techniques. Stated another way, it is a culture wherein virtually all of the bacterial cells present are of the selected strain.

The term "rhizosphere" is used interchangeably with "root zone" to denote that segment of the soil that surrounds the roots of a plant and is influenced by them.

The term "inoculant" as described in this invention is defined in several Federal, or State regulations as (1) "soil or plant inoculants shall include any carrier or culture of a specific micro-organism or mixture of micro-organisms represented to improve the soil or the growth, quality, or yield of plants, and shall also include any seed or fertilizer represented to be inoculated with such a culture" (New York State 10-A Consolidated Law); (2) "substances other than fertilizers, manufactured, sold or represented for use in the improvement of the physical condition of the soil or to aid plant growth or crop yields" (Canada Fertilizers Act); (3) "a formulation containing pure or predetermined mixtures of living bacteria, fungi or virus particles for the treatment of seed, seedlings or other plant propagation material for the purpose of enhancing the growth capabilities or disease resistance or otherwise altering the properties of the eventual plants or crop" (Ad hoc European Working Group, 1997) or (4) "meaning any chemical or biological substance of mixture of substances or device distributed in this state to be applied to soil, plants or seeds for soil corrective purposes; or which is intended to improve germination, growth, quality, yield, product quality, reproduction, flavor, or other desirable characteristics of plants or which is intended to produce any chemical, biochemical, biological or physical change in soil" (Section 14513 of the California Food and Agriculture Code).

The term "effective amount" refers to a quantity which is sufficient to result in a statistically significant increase of growth and/or of protein yield and/or of grain yield of a plant as compared to the growth, protein yield and grain yield of the control-treated plant.

The terms "agriculturally acceptable carrier" and "carrier" are used interchangeably herein.

The terms "promoting plant growth" and "stimulating plant growth" are used interchangeably herein, and refer to the ability to enhance or increase at least one of the plant's height, weight, leaf size, root size, or stem size, to increase protein yield from the plant or to increase grain yield of the plant.

DETAILED DESCRIPTION

The present invention relates to biologically pure bacterial cultures of plant growth-promoting bacteria (PGPB) wherein the bacteria, i.e. the bacterial strain in each of the bacterial cultures, are selected from the group consisting of (a) *Bacillus aryabhattai* strain CAP53 (NRRL No. B-50819), (b) *Bacillus aryabhattai* strain CAP56 (NRRL No. B-50817), (c) *Bacillus flexus* strain BT054 (NRRL No. B-50816), (d) *Paracoccus kondratievae* strain NC35 (NRRL No. B-50820), (e) *Bacillus mycoides* strain BT155 (NRRL No. B-50921), (f) *Enterobacter cloacae* strain CAP12 (NRRL No. B-50822), (g) *Bacillus nealsonii* strain BOBA57 (NRRL No. B-50821), (h) *Bacillus mycoides* strain EE118 (NRRL No. B-50918), (i) *Bacillus subtilis* strain EE148 (NRRL No. B-50927), (j) *Alcaligenes faecalis* strain EE107 (NRRL No. B-50920), (k) *Bacillus mycoides* strain EE141 (NRRL No. B-50916), (l) *Bacillus mycoides* strain BT46-3 (NRRL No. B-50922), (m) *Bacillus cereus* family member strain EE128 (NRRL No. B-50917), (n) *Bacillus thuringiensis* strain BT013A (NRRL No. B-50924), (o) *Paenibacillus massiliensis* strain BT23 (NRRL No. B-50923), (p) *Bacillus cereus* family member strain EE349 (NRRL No. B-50928), (q) *Bacillus subtilis* strain EE218 (NRRL No. B-50926), (r) *Bacillus megaterium* strain EE281 (NRRL No. B-50925), (s) salt-tolerant and thiram-resistant *Paracoccus* sp. NC35 (NRRL No. B-50948), (t) salt-tolerant and thiram-resistant *Bacillus mycoides* strain BT155 (NRRL No. B-50949), (u) thiram-resistant *Bacillus aryabhattai* CAP53 (NRRL No. B-50946), (v) thiram-resistant *Bacillus thuringiensis* BT013A (NRRL No. B-50947), or (w) glyphosate-tolerant *Bacillus aryabhattai* CAP53 (NRRL No. B-50945).

The foregoing strains (a)-(d) and (f)-(g) were deposited with the United States Department of Agriculture (USDA) Agricultural Research Service (ARS), having the address 1815 North University Street, Peoria, Ill. 61604 U.S.A., on Mar. 7, 2013, and are identified by the NRRL numbers provided in parentheses. The strains (e) and (h)-(r) were deposited with the United States Department of Agriculture (USDA) Agricultural Research Service (ARS) on Mar. 10, 2014, and are also identified by the NRRL numbers provided in parentheses. The strains (s)-(w) were deposited with the United States Department of Agriculture (USDA) Agricultural Research Service (ARS) on Mar. 17, 2014, and are also identified by the NRRL numbers provided in parentheses.

As shown in the Examples, the present strains were isolated from rhizospheres of various vigorous plants, and were shown to be most promising among a large number of isolates by in vitro culturing and application to plants. The novel strains disclosed herein were identified by 16S RNA sequencing and biochemical assays. Thus, *Bacillus aryabhattai* strain CAP53 has a 16S ribosomal RNA sequence having at least about 98%, at least about 99%, or 100% sequence identity with the sequence of SEQ ID NO: 1; *Bacillus aryabhattai* strain CAP56 has a 16S ribosomal RNA sequence having at least about 98%, at least about 99%, or 100% sequence identity with the sequence of SEQ ID NO: 2; *Bacillus flexus* strain BT054 has a 16S ribosomal RNA sequence having at least about 98%, at least about 99%, or 100% sequence identity with the sequence of SEQ ID NO: 3; *Paracoccus kondratievae* strain NC35 has a 16S ribosomal RNA sequence having at least about 98%, at least about 99%, or 100% sequence identity with the sequence of SEQ ID NO: 4; *Bacillus mycoides* strain BT155 (NRRL No. B-50921) has a 16S ribosomal RNA sequence having at least about 98%, at least about 99%, or 100% sequence identity with the sequence of SEQ ID NO: 21; *Enterobacter cloacae* strain CAP12 has a 16S ribosomal RNA sequence having at least about 98%, at least about 99%, or 100% sequence identity with the sequence of SEQ ID NO: 5; *Bacillus nealsonii* strain BOBA57 has a 16S ribosomal RNA sequence having at least about 98%, at least about 99%, or 100% sequence identity with the sequence of SEQ ID NO: 6; *Bacillus mycoides* strain EE118 has a 16S ribosomal RNA sequence having at least about 98%, at least about 99%, or 100% sequence identity with the sequence of SEQ ID NO: 10; *Bacillus subtilis* strain EE148 has a 16S ribosomal RNA sequence having at least about 98%, at least about 99%, or 100% sequence identity with the sequence of SEQ ID NO: 11; *Alcaligenes faecalis* strain EE107 has a 16S ribosomal RNA sequence having at least about 98%, at least about 99%, or 100% sequence identity with the sequence of SEQ ID NO: 12; *Bacillus mycoides* strain EE141 has a 16S ribosomal RNA sequence having at least about 98%, at least about 99%, or 100% sequence identity with the sequence of SEQ ID NO: 13; *Bacillus mycoides* strain BT46-3 has a 16S ribosomal RNA sequence having at least about 98%, at least about 99%, or 100% sequence identity with the sequence of SEQ ID NO: 14; *Bacillus cereus* family member strain EE128 has a 16S ribosomal RNA sequence having at least about 98%, at least about 99%, or 100% sequence identity with the sequence of SEQ ID NO: 15; *Bacillus thuringeiensis* strain BT013A has a 16S ribosomal RNA sequence having at least about 98%, at least about 99%, or 100% sequence identity with the sequence of SEQ ID NO: 16; *Paenibacillus massiliensis* strain BT23 has a 16S ribosomal RNA sequence having at least about 98%, at least about 99%, or 100% sequence identity with the sequence of SEQ ID NO: 17; *Bacillus cereus* family member strain EE349 has a 16S ribosomal RNA sequence having at least about 98%, at least about 99%, or 100% sequence identity with the sequence of SEQ ID NO: 18; *Bacillus subtilis* strain EE218 has a 16S ribosomal RNA sequence having at least about 98%, at least about 99%, or 100% sequence identity with the sequence of SEQ ID NO: 19; and *Bacillus megaterium* strain EE281 has a 16S ribosomal RNA sequence having at least about 98%, at least about 99%, or 100% sequence identity with the sequence of SEQ ID NO: 20. These sequences are shown in Table 1 below.

TABLE 1

| Strain (SEQ ID. NO) | Partial 16S ribosomal RNA sequence |
|---|---|
| *Bacillus aryabhattai* CAP53 (SEQ ID NO: 1) | GGNNCAACGCCGCGTGAGTGATGAAGGCTTTCGGGTCGTAAAACT CTGTTGTTAGGGAAGAACAAGTACGAGAGTAACTGCTCGTACCTT GACGGTACCTAACCAGAAAGCCACGGCTAACTACGTGCCAGCAGC CGCGGTAATACGTAGGTGGCAAGCGTTATCCGGAATTATTGGGCG TAAAGCGCGCGCAGGCGGTTTCTTAAGTCTGATGTGAAAGCCCAC GGCTCAACCGTGGAGGGTCATTGGAAACTGGGGAACTTGAGTGCA GAAGAGAAAAGCGGAATTCCACGTGTAGCGGTGAAATGCGTAGAG ATGTGGAGGAACACCAGTGGCGAAGGCGGCTTTTTGGTCTGTAAC TGACGCTGAGGCGCGAAAGCGTGGGGAGCAAACAGGATTAGATAC CCTGGTAGTCCACGCCGTAAACGATGAGTGCTAAGTGTTAGAGGG TTTCCGCCCTTTAGTGCTGCAGCTAACGCATTAAGCACTCCGCCTG GGGAGTACGGTCGCAAGACTGAAACTCAAAGGAATTGACGGGGGC CCGCACAAGCGGTGGAGCATGTGGTTTAATTCGAAGCAACGCGAA GAACCTTACCAGGTCTTGACATCCTCTGACAACTCTAGAGATAGAG CGTTCCCCTTCGGGGGACAGAGTGACAGGTGGTGCATGGTTGTCGT CAGCTCGTGTCGTGAGATGTTGGGTTAAGTCCCGCAACG |
| *Bacillus aryabhattai* CAP56 (SEQ ID NO: 2) | TCTGANGGNNCACGCCGCGTGAGTGATGAAGGCTTTCGGGTCGTA AAACTCTGTTGTTAGGGAAGAACAAGTACGAGAGTAACTGCTCGT ACCTTGACGGTACCTAACCAGAAAGCCACGGCTAACTACGTGCCA GCAGCCGCGGTAATACGTAGGTGGCAAGCGTTATCCGGAATTATT GGGCGTAAAGCGCGCGCAGGCGGTTTCTTAAGTCTGATGTGAAAG CCCACGGCTCAACCGTGGAGGGTCATTGGAAACTGGGGAACTTGA GTGCAGAAGAGAAAAGCGGAATTCCACGTGTAGCGGTGAAATGCG TAGAGATGTGGAGGAACACCAGTGGCGAAGGCGGCTTTTTGGTCT GTAACTGACGCTGAGGCGCGAAAGCGTGGGGAGCAAACAGGATTA GATACCCTGGTAGTCCACGCCGTAAACGATGAGTGCTAAGTGTTA GAGGGTTTCCGCCCTTTAGTGCTGCAGCTAACGCATTAAGCACTCC GCCTGGGGAGTACGGTCGCAAGACTGAAACTCAAAGGAATTGACG GGGGCCCGCACAAGCGGTGGAGCATGTGGTTTAATTCGAAGCAAC GCGAAGAACCTTACCAGGTCTTGACATCCTCTGACAACTCTAGAGA TAGAGCGTTCCCCTTCGGGGGACAGAGTGACAGGTGGTGCATGGT TGTCGTCAGCTCGTGTCGTGAGATGTTGGGTTAAGTCCCGC |
| *Bacillus flexus* BT054 (SEQ ID NO: 3) | GGANCAACGCCGCGTGAGTGANGAAGGCTTTCGGGTCGTAAAACT CTGTTGTTAGGGAAGAACAAGTACAAGAGTAACTGCTTGTACCTTG ACGGTACCTAACCAGAAAGCCACGGCTAACTACGTGCCAGCAGCC GCGGTAATACGTAGGTGGCAAGCGTTATCCGGAATTATTGGGCGT AAAGCGCGCGCAGGCGGTTTCTTAAGTCTGATGTGAAAGCCCACG GCTCAACCGTGGAGGGTCATTGGAAACTGGGGAACTTGAGTGCAG AAGAGAAAAGCGGAATTCCACGTGTAGCGGTGAAATGCGTAGAGA TGTGGAGGAACACCAGTGGCGAAGGCGGCTTTTTGGTCTGTAACT GACGCTGAGGCGCGAAAGCGTGGGGAGCAAACAGGATTAGATAC CCTGGTAGTCCACGCCGTAAACGATGAGTGCTAAGTGTTAGAGGG TTTCCGCCCTTTAGTGCTGCAGCTAACGCATTAAGCACTCCGCCTG GGGAGTACGGTCGCAAGACTGAAACTCAAAGGAATTGACGGGGGC CCGCACAAGCGGTGGAGCATGTGGTTTAATTCGAAGCAACGCGAA GAACCTTACCAGGTCTTGACATCCTCTGACAACTCTAGAGATAGAG CGTTCCCCTTCGGGGGACAGAGTGACAGGTGGTGCATGGTTGTCGT CAGCTCGTGTCGTGAGATGTTGGGTTAAGTCCCGCAAC |
| *Paracoccus kondratievae* NC35 (SEQ ID NO: 4) | GCCGCGTGAGTGNNNAAGNCCCTAGGGTTGTAAAGCTCTTTCANC TGGGAAGATAATGACTGTACCAGCAGAAGAAGCCCCGGCTAACTC CGTGCCAGCAGCCGCGGTAATACGGAGGGGCTAGCGTTGTTCGG AATTACTGGGCGTAAAGCGCACGTAGGCGGACCGGAAAGTTGGGG GTGAAATCCCGGGGCTCAACCCCGGAACTGCCTTCAAAACTATCG GTCTGGAGTTCGAGAGAGGTGAGTGGAATTCCGAGTGTAGAGGTG AAATTCGTAGATATTCGGAGGAACACCAGTGGCGAAGGCGGCTCA CTGGCTCGATACTGACGCTGAGGTGCGAAAGCGTGGGGAGCAAAC AGGATTAGATACCCTGGTAGTCCACGCCGTAAACGATGAATGCCA GTCGTCGGGCAGCATGCTGTTCGGTGACACACCTAACGGATTAAG CATTCCGCCTGGGGAGTACGGTCGCAAGATTAAAACTCAAAGGAA TTGACGGGGGCCCGCACAAGCGGTGGAGCATGTGGTTTAATTCGA AGCAACGCGCAGAACCTTACCAACCCTTGACATCCCAGGACAGCC |

TABLE 1-continued

| Strain (SEQ ID. NO) | Partial 16S ribosomal RNA sequence |
|---|---|
| | CGAGAGATCGGGTCTCCACTTCGGTGGCCTGGAGACAGGTGCTGC<br>ATGGCTGTCGTCAGCTCGTGTCGTGAGATGTTCGGTTAAGTCCGGC |
| Enterobacter cloacae CAP12 (SEQ ID NO: 5) | CTGNNGCAGCCNTGCCGCGTGTATGAAGAAGGNCTTCGGGTTGTA<br>AAGTACTTTCAGCGGGGAGGAAGGTGTTGTGGTTAATAACCACAG<br>CAATTGACGTTACCCGCAGAAGAAGCACCGGCTAACTCCGTGCCA<br>GCAGCCGCGGTAATACGGAGGGTGCAAGCGTTAATCGGAATTACT<br>GGGCGTAAAGCGCACGCAGGCGGTCTGTCAAGTCGGATGTGAAAT<br>CCCCGGGCTCAACCTGGGAACTGCATTCGAAACTGGCAGGCTAGA<br>GTCTTGTAGAGGGGGGTAGAATTCCAGGTGTAGCGGTGAAATGCG<br>TAGAGATCTGGAGGAATACCGGTGGCGAAGGCGGCCCCCTGGACA<br>AAGACTGACGCTCAGGTGCGAAAGCGTGGGGAGCAAACAGGATTA<br>GATACCCTGGTAGTCCACGCCGTAAACGATGTCGATTTGGAGGTTG<br>TGCCCTTGAGGCGTGGCTTCCGGAGCTAACGCGTTAAATCGACCGC<br>CTGGGGAGTACGGCCGCAAGGTTAAAACTCAAATGAATTGACGGG<br>GGCCCGCACAAGCGGTGGAGCATGTGGTTTAATTCGATGCAACGC<br>GAAGAACCTTACCTGGTCTTGACATCCACAGAACTTTCCAGAGATG<br>GATTGGTGCCTTCGGGAACTGTGAGACAGGTGCTGCATGGCTGTCG<br>TCAGCTCGTGTTGTGAAATGTTGGGTTAAGTCCCGCAACNANNCGC<br>AAC |
| Bacillus nealsonii BOBA57 (SEQ ID NO: 6) | TGNNGGANCAACGCCGCGTGAGTGATGAAGGTTTTCGGATCGTAA<br>AACTCTGTTGTTAGGGAAGAACAAGTACGAGAGTAACTGCTCGTA<br>CCTTGACGGTACCTAACCAGAAAGCCACGGCTAACTACGTGCCAG<br>CAGCCGCGGTAATACGTAGGTGGCAAGCGTTGTCCGGAATTATTG<br>GGCGTAAAGCGCGCGCAGGCGGTCCTTTAAGTCTGATGTGAAAGC<br>CCACGGCTCAACCGTGGAGGGTCATTGGAAACTGGGGGACTTGAG<br>TGCAGAAGAGAAGAGTGGAATTCCACGTGTAGCGGTGAAATGCGT<br>AGAGATGTGGAGGAACACCAGTGGCGAAGGCGACTCTTTGGTCTG<br>TAACTGACGCTGAGGCGCGAAAGCGTGGGGAGCAAACAGGATTAG<br>ATACCCTGGTAGTCCACGCCGTAAACGATGAGTGCTAAGTGTTAG<br>AGGGTTTCCGCCCTTTAGTGCTGCAGCAAACGCATTAAGCACTCCG<br>CCTGGGGAGTACGGCCGCAAGGCTGAAACTCAAAGGAATTGACGG<br>GGGCCCGCACAAGCGGTGGAGCATGTGGTTTAATTCGAAGCAACG<br>CGAAGAACCTTACCAGGTCTTGACATCTCCTGACAATCCTAGAGAT<br>AGGACGTTCCCCTTCGGGGACAGGATGACAGGTGGTGCATGGTT<br>GTCGTCAGCTCGTGTCGTGAGATGTTGGGTTAAGTCCCGC |
| Bacillus mycoides EE118 (SEQ ID NO: 10) | GGAGCACGCCGCGTGAGTGNNGAAGGCTTTCGGGTCGTAAAACTC<br>TGTTGTTAGGGAAGAACAAGTGCTAGTTGAATAAGCTGGCACCTT<br>GACGGTACCTAACCAGAAAGCCACGGCTAACTACGTGCCAGCAGC<br>CGCGGTAATACGTAGGTGGCAAGCGTTATCCGGAATTATTGGGCG<br>TAAAGCGCGCGCAGGTGGTTTCTTAAGTCTGATGTGAAAGCCCAC<br>GGCTCAACCGTGGAGGGTCATTGGAAACTGGGAGACTTGAGTGCA<br>GAAGAGGAAAGTGGAATTCCATGTGTAGCGGTGAAATGCGTAGAG<br>ATATGGAGGAACACCAGTGGCGAAGGCGACTTTCTGGTCTGTAAC<br>TGACACTGAGGCGCGAAAGCGTGGGGAGCAAACAGGATTAGATAC<br>CCTGGTAGTCCACGCCGTAAACGATGAGTGCTAAGTGTTAGAGGG<br>TTTCCGCCCTTTAGTGCTGAAGTTAACGCATTAAGCACTCCGCCTG<br>GGGAGTACGGCCGCAAGGCTGAAACTCAAAGGAATTGACGGGGG<br>CCCGCACAAGCGGTGGAGCATGTGGTTTAATTCGAAGCAACGCGA<br>AGAACCTTACCAGGTCTTGACATCCTCTGAAAACTCTAGAGATAGA<br>GCTTCTCCTTCGGGAGCAGAGTGACAGGTGGTGCATGGTTGTCGTC<br>AGCTCGTGTCGTGAGATGTTGGGTTAAGTCCCGC |
| Bacillus subtilis EE148 (SEQ ID NO: 11) | CGCCGCGTGAGTGATGAAGGTTTTCGGATCGTAAAGCTCTGTTGTT<br>AGGGAAGAACAAGTGCCGTTCAAATAGGGCGGCACCTTGACGGTA<br>CCTAACCAGAAAGCCACGGCTAACTACGTGCCAGCAGCCGCGGTA<br>ATACGTAGGTGGCAAGCGTTGTCCGGAATTATTGGGCGTAAAGGG<br>CTCGCAGGCGGTTTCTTAAGTCTGATGTGAAAGCCCCCGGCTCAAC<br>CGGGGAGGGTCATTGGAAACTGGGGAACTTGAGTGCAGAAGAGG<br>AGAGTGGAATTCCACGTGTAGCGGTGAAATGCGTAGAGATGTGGA<br>GGAACACCAGTGGCGAAGGCGACTCTCTGGTCTGTAACTGACGCT<br>GAGGAGCGAAAGCGTGGGGAGCGAACAGGATTAGATACCCTGGT<br>AGTCCACGCCGTAAACGATGAGTGCTAAGTGTTAGGGGGTTTCCG<br>CCCCTTAGTGCTGCAGCTAACGCATTAAGCACTCCGCCTGGGGAGT<br>ACGGTCGCAAGACTGAAACTCAAAGGAATTGACGGGGGCCCGCAC<br>AAGCGGTGGAGCATGTGGTTTAATTCGAAGCAACGCGAAGAACCT<br>TACCAGGTCTTGACATCCTCTGACAATCCTAGAGATAGGACGTCCC<br>CTTCGGGGCAGAGTGACAGGTGGTGCATGGTTGTCGTCAGCTCGT<br>GTCGTGAGATGTTGGGTTAAGTCC |
| Alcaligenes faecalis EE107 (SEQ ID NO: 12) | CTTCGGGTTGTAAAGTACTTTTGGCAGAGAAGAAAAGGTATCTCCT<br>AATACGAGATACTGCTGACGGTATCTGCAGAATAAGCACCGGCTA<br>ACTACGTGCCANCAGCCGCGGTAATACGTAGGGTGCAAGCGTTAA<br>TCGGAATTACTGGGCGTAAAGCGTGTGTAGGCGGTTCGGAAAGAA<br>AGATGTGAAATCCCAGGGCTCAACCTTGGAACTGCATTTTTAACTG |

TABLE 1-continued

| Strain (SEQ ID. NO) | Partial 16S ribosomal RNA sequence |
|---|---|
| | CCGAGCTAGAGTATGTCAGAGGGGGTAGAATTCNNNTGTAGCAN NGAAATGCGTAGATATGTGGAGGAATACCGATGGCGAAGGCAGCC CCCTGGGATAATACTGACGCTCAGACACGAAAGCGTGGGGAGCAA ACAGGATTAGATACCCTGGTAGTCCACGCCCTAAACGATGTCAACT AGCTGTTGGGGCCGTTAGGCCTTAGTAGCGCAGCTAACGCGTGAA GTTGACCGCCTGGGGAGTACGGTCGCAAGATTAAAACTCAAAGGA ATTGACGGGGACCCGCACAAGCGGTGGATGATGTGGATTAATTCG ATGCAACGCGAAAAACCTTACCTACCCTTGACATGTCTGGAAAGC CGAAGAGATTTGGCCGTGCTCGCAAGAGAACCGGAACACAGGTGC TGCATGGCTGTCGTCAGCTCGTGTCGTGAGATGTTGGGTTAAGTCC C |
| Bacillus mycoides EE141 (SEQ ID NO: 13) | AAAGTCTGACGGAGCACGCCGCGTGAGTGATGAAGGCTTTCGGGT CGTAAAACTCTGTTGTTAGGGAAGAACAAGTGCTAGTTGAATAAG CTGGCACCTTGACGGTACCTAACCAGAAAGCCACGGCTAACTACG TGCCAGCAGCCGCGGTAATACGTAGGTGGCAAGCGTTATCCGGAA TTATTGGGCGTAAAGCGCGCGCAGGTGGTTTCTTAAGTCTGATGTG AAAGCCCACGGCTCAACCGTGGAGGGTCATTGGAAACTGGGAGAC TTGAGTGCAGAAGAGGAAAGTGGAATTCCATGTGTAGCGGTGAAA TGCGTAGAGATATGGAGGAACACCAGTGGCGAAGGCGACTTTCTG GTCTGTAACTGACACTGAGGCGCGAAAGCGTGGGGAGCAAACAGG ATTAGATACCCTGGTAGTCCACGCCGTAAACGATGAGTGCTAAGT GTTAGAGGGTTTCCGCCCTTTAGTGCTGAAGTTAACGCATTAAGCA CTCCGCCTGGGGAGTACGGCCGCAAGGCTGAAACTCAAAGGAAT TGACGGGGGCCCGCACAAGCGGTGGAGCATGTGGTTTAATTCGAA GCAACGCGAAGAACCTTACCAGGTCTTGACATCCTCTGAAAACNC TAGAGATANNNCTTCTCCTTCGGGAGCAGAGTGACAGGTGGTGCA TGGTTGTCGTCAGCTCGTGTCGTGAGATGTTGGGTTAAGTCCC |
| Bacillus mycoides BT46-3 (SEQ ID NO: 14) | GGAGCACGCCGCGTGAGTGATGAAGGCTTTCGGGTCGTAAAACTC TGTTGTTAGGGAAGAACAAGTGCTAGTTGAATAAGCTGGCACCTT GACGGTACCTAACCAGAAAGCCACGGCTAACTACGTGCCAGCAGC CGCGGTAATACGTAGGTGGCAAGCGTTATCCGGAATTATTGGGCG TAAAGCGCGCGCAGGTGGTTTCTTAAGTCTGATGTGAAAGCCCAC GGCTCAACCGTGGAGGGTCATTGGAAACTGGGAGACTTGAGTGCA GAAGAGGAAAGTGGAATTCCATGTGTAGCGGTGAAATGCGTAGAG ATATGGAGGAACACCAGTGGCGAAGGCGACTTTCTGGTCTGTAAC TGACACTGAGGCGCGAAAGCGTGGGGAGCAAACAGGATTAGATAC CCTGGTAGTCCACGCCGTAAACGATGAGTGCTAAGTGTTAGAGGG TTTCCGCCCTTTAGTGCTGAAGTTAACGCATTAAGCACTCCGCCTG GGGAGTACGGCCGCAAGGCTGAAACTCAAAGGAATTGACGGGGG CCCGCACAAGCGGTGGAGCATGTGGTTTAATTCGAAGCAACGCGA AGAACCTTACCAGGTCTTGACATCCTCTGACAACCCTAGAGATAGG GCTTCCCCTTCGGGGGCAGAGTGACAGGTGGTGCATGGTTGTCGTC AGCTCGTGTCGTGAGATGTTGGGTTAAGTCCC |
| Bacillus cereus family member EE128 (SEQ ID NO: 15) | GGANCAACGCCGCGTGAGTGANGAAGGCTTTCGGGTCGTAAAACT CTGTTGTTAGGGAAGAACAAGTGCTAGTTGAATAAGCTGGCACCTT GACGGTACCTAACCAGAAAGCCACGGCTAACTACGTGCCAGCAGC CGCGGTAATACGTAGGTGGCAAGCGTTATCCGGAATTATTGGGCG TAAAGCGCGCGCAGGTGGTTTCTTAAGTCTGATGTGAAAGCCCAC GGCTCAACCGTGGAGGGTCATTGGAAACTGGGAGACTTGAGTGCA GAAGAGGAAAGTGGAATTCCATGTGTAGCGGTGAAATGCGTAGAG ATATGGAGGAACACCAGTGGCGAAGGCGACTTTCTGGTCTGTAAC TGACACTGAGGCGCGAAAGCGTGGGGAGCAAACAGGATTAGATAC CCTGGTAGTCCACGCCGTAAACGATGAGTGCTAAGTGTTAGAGGG TTTCCGCCCTTTAGTGCTGAAGTTAACGCATTAAGCACTCCGCCTG GGGAGTACGGCCGCAAGGCTGAAACTCAAAGGAATTGACGGGGG CCCGCACAAGCGGTGGAGCATGTGGTTTAATTCGAAGCAACGCGA AGAACCTTACCAGGTCTTGACATCCTCTGAAAACTCTAGAGATAGA GCTTCTCCTTCGGGAGCAGAGTGACAGGTGGTGCATGGTTGTCGTC AGCTCGTGTCGTGAGATGNTGGGTTAAGTCCCGCA |
| Bacillus thuringiensis BT013A (SEQ ID NO: 16) | TCTGACGGAGCAACGCCGCGTGAGTGATGAAGGCTTTCGGGTCGT AAAACTCTGTTGTTAGGGAAGAACAAGTGCTAGTTGAATAAGCTG GCACCTTGACGGTACCTAACCAGAAAGCCACGGCTAACTACGTGC CAGCAGCCGCGGTAATACGTAGGTGGCAAGCGTTATCCGGAATTA TTGGGCGTAAAGCGCGCGCAGGTGGTTTCTTAAGTCTGATGTGAAA GCCCACGGCTCAACCGTGGAGGGTCATTGGAAACTGGGAGACTTG AGTGCAGAAGAGGAAAGTGGAATTCCATGTGTAGCGGTGAAATGC GTAGAGATATGGAGGAACACCAGTGGCGAAGGCGACTTTCTGGTC TGTAACTGACACTGAGGCGCGAAAGCGTGGGGAGCAAACAGGATT AGATACCCTGGTAGTCCACGCCGTAAACGATGAGTGCTAAGTGTT AGAGGGTTTCCGCCCTTTAGTGCTGAAGTTAACGCATTAAGCACTC CGCCTGGGGAGTACGGCCGCAAGGCTGAAACTCAAAGGAATTGAC GGGGGCCCGCACAAGCGGTGGAGCATGTGGTTTAATTCGAAGCAA CGCGAAGAACCTTACCAGGTCTTGACATCCTCTGAAAACCCTAGA |

TABLE 1-continued

| Strain (SEQ ID. NO) | Partial 16S ribosomal RNA sequence |
|---|---|
| | GATAGGGCTTCTCCTTCGGGAGCAGAGTGACAGGTGGTGCATGGT TGTCGTCAGCTCGTGTCGTGAGATGTTGGGTTAAGTCCCGCAACGA GCGCAACCCTTGATCTTAGTTGCCATCATTAAGTTGGGCACTCTAA GGTGACTGCCGGTGACAAACCGGAGGAAGGTGGGGATGACGTCAA ATCATCATGCCCCTTATGACCTGGGCTACACACGTGCTACAATGGA CGGTACAAAGAGCTGC |
| Paenibacillus massiliensis BT23 (SEQ ID NO: 17) | CTTANNGNNTGANNNNNCTTGNNAANAAAGCCCCGGCTAACTACN TGCCANCANCCGCGGTAATACNTANGGNGCAAGCGTTGTCCGGAA TTATTGGGCGTAAAGCGCGCGCAGGCGGTCNTTTAAGTCTGGTGTT TAAGCCCGGGGCTCAACCCCGGATCNCNCGGGAAACTGGATGACT TGANTGCNNAANAAGAGAGTGGAATTCCNNGTGTANCGGTGAAAT GCNTANANATGTGNANGAACACCANTGGCNAANGCNACTCTCTGG GCTGTAACTGACNCTGANGCNCGAAAGCGTGGGGAGCAAACANG ATTANATACCCTGGTANTCCACGCCNTANACNATNANTGCTAGGT GTTNNGGGTTTCNATACCCTTGNTGCCNAANTTAACACATTAANCA CTCCGCCTGGNNANTACNGTCNCAANANTGAAACTCNNANGAANT GACNGGGACCCGCACAAGCNNTGNANTATGTGGTTTAANTNNNNN CAACNCNAANAANCTTACCNNGNCTTGACATCTNAATGACCNGNG CANANATGTNCCTTTCCTTCNGNACATTCNNGACAGGTGGTGCATG GNTGTCNTCNNCTCNTGTCNNGNGATGTTGGGTTAANTCCCCGCAN CNANNNN |
| Bacillus cereus family member EE349 (SEQ ID NO: 18) | AAGGCTTTCGGGTCGTAAAACTCTGTTGTTAGGGAAGAACAAGTG CTAGTTGAATAAGCTGGCACCTTGACGGTACCTAACCAGAAAGCC ACGGCTAACTACGTGCCAGCAGCCGCGGTAATACGTAGGTGGCAA GCGTTATCCGGAATTATTGGGCGTAAAGCGCGCGCAGGTGGTTTCT TAAGTCTGATGTGAAAGCCCACGGCTCAACCGTGGAGGGTCATTG GAAACTGGGAGACTTGAGTGCAGAAGAGGAAAGTGGAATTCCATG TGTAGCGGTGAAATGCGTAGAGATATGGAGGAACACCAGTGGCGA AGGCGACTTTCTGGTCTGTAACTGACACTGAGGCGCGAAAGCGTG GGGAGCAAACAGGATTAGATACCCTGGTAGTCCACGCCGTAAACG ATGAGTGCTAAGTGTTAGAGGGTTTCCGCCCTTTAGTGCTGAAGTT AACGCATTAAGCACTCCGCCTGGGGAGTACGGCCGCAAGGCTGAA ACTCAAAGGAATTGACGGGGGCCCGCACAAGCGGTGGAGCATGTG GTTTAATTCGAAGCAACGCGAAGAACCTTACCAGGTCTTGACATCC TCTGAAAACCCTAGAGATAGGGCTTCTCCTTCGGGAGCAGAGTGA CAGGTGGTGCATGGTTGTCGTCAGCTCGTGTCGTGAGATGTTGGGT TAAGTCC |
| Bacillus subtilis EE218 (SEQ ID NO: 19) | AAGCTCTGTTGTTAGGGAAGAACAAGTACCGTTCGAATAGGGCGG TACCTTGACGGTACCTAACCAGAAAGCCACGGCTAACTACGTGCC AGCAGCCGCGGTAATACGTAGGTGGCAAGCGTTGTCCGGAATTAT TGGGCGTAAAGGGCTCGCAGGCGGTTTCTTAAGTCTGATGTGAAA GCCCCCGGCTCAACCGGGGAGGGTCATTGGAAACTGGGGAACTTG AGTGCAGAAGAGGAGAGTGGAATTCCACGTGTAGCGGTGAAATGC GTAGAGATGTGGAGGAACACCAGTGGCGAAGGCGACTCTCTGGTC TGTAACTGACGCTGAGGAGCGAAAGCGTGGGGAGCGAACAGGATT AGATACCCTGGTAGTCCACGCCGTAAACGATGAGTGCTAAGTGTT AGGGGGTTTCCGCCCCTTANTGCTGCAGCTAACGCATTAAGCACTC CGCCTGGGGAGTACGGTCGCAAGACTGAAACTCAAAGGAATTGAC GGGGGCCCGCACAAGCGGTGGAGCATGTGGTTTAATTCGAAGCAA CGCGAANAACCTTACCAGGTCTTGACATCCTCTGACAATCCTAGAG ATAGGACGTCCCCTTCGGGGCAGAGTGACAGGTGGTGCATGGTT GTCGTCANCTCGTGTCGTGAGATGTTGGNTAAGTCCCGCAACGAG |
| Bacillus megaterium EE281 (SEQ ID NO: 20) | AAGNCTTTCGGNNCGTAAAACTCTGTTGTTAGGGAAGAACAAGTA CGAGAGTAACTGCTCGTACCTTGACGGTACCTAACCAGAAAGCCA CGGCTAACTACGTGCCAGCAGCCGCGGTAATACGTAGGTGGCAAG CGTTATCCGGAATTATTGGGCGTAAAGCGCGCGCAGGCGGTTCTT AAGTCTGATGTGAAAGCCCACGGCTCAACCGTGGAGGGTCATTGG AAACTGGGGAACTTGAGTGCAGAAGAGAAAAGCGGAATTCCACGT GTAGCGGTGAAATGCGTAGAGATGTGGAGGAACACCAGTGGCGAA GGCGGCTTTTTGGTCTGTAACTGACGCTGAGGCGCGAAAGCGTGG GGAGCAAACAGGATTAGATACCCTGGTAGTCCACGCCGTAAACGA TGAGTGCTAAGTGTTAGAGGGTTTCCGCCCTTTAGTGCTGCAGCTA ACGCATTAAGCACTCCGCCTGGGGAGTACGGTCGCAAGACTGAAA CTCAAAGGAATTGACGGGGGCCCGCACAAGCGGTGGAGCATGTGG TTTAATTCGAAGCAACGCGAAGAACCTTACCAGGTCTTGACATCCT CTGACAACTCTAGAGATAGAGCGTTCCCCTTCGGGGACAGAGTG ACAGGTGGTGCATGGTTGTCGTCAGCTCGTGTCGTGAGATGTTGGG TTAAGTCCCNNNCNNNNNNNNNNNNNNNNNTCTNAGANNCGNGCT GACNANNCCANGCACCNNGG |
| Bacillus mycoides BT155 | GTCTGANGGANCACGCCGCGTGAGTGATGAAGGCTTTCGGGTCGT AAAACTCTGTTGTTAGGGAAGAACAAGTGCTAGTTGAATAAGCTG GCACCTTGACGGTACCTAACCAGAAAGCCACGGCTAACTACGTGC |

TABLE 1-continued

| Strain (SEQ ID. NO) | Partial 16S ribosomal RNA sequence |
|---|---|
| (SEQ ID NO: 21) | CAGCAGCCGCGGTAATACGTAGGTGGCAAGCGTTATCCGGAATTA<br>TTGGGCGTAAAGCGCGCGCAGGTGGTTTCTTAAGTCTGATGTGAAA<br>GCCCACGGCTCAACCGTGGAGGGTCATTGGAAACTGGGAGACTTG<br>AGTGCAGAAGAGGAAAGTGGAATTCCATGTGTAGCGGTGAAATGC<br>GTAGAGATATGGAGGAACACCAGTGGCGAAGGCGACTTTCTGGTC<br>TGTAACTGACACTGAGGCGCGAAAGCGTGGGGAGCAAACAGGATT<br>AGATACCCTGGTAGTCCACGCCGTAAACGATGAGTGCTAAGTGTT<br>AGAGGGTTTCCGCCCTTTAGTGCTGAAGTTAACGCATTAAGCACTC<br>CGCCTGGGGAGTACGGCCGCAAGGCTGAAACTCAAAGGAATTGAC<br>GGGGGCCCGCACAAGCGGTGGAGCATGTGGTTTAATTCGAAGCAA<br>CGCGAAGAACCTTACCAGGTCTTGACATCCTCTGACAACCCTAGAG<br>ATAGGGCTTCCCCTTCGGGGGCAGAGTGACAGGTGGTGCATGGTT<br>GTCGTCAGCTCGTGTCGTGAGATGTTGGGTTAAGTCCCG |

Methods for determining sequence identity are well known by one of ordinary skill in the art. By way of example and not of limitation, the BLASTn algorithm available through National Center for Biotechnology Information (NCBI) can be used to align sequences and determine their identity.

The foregoing bacterial strains were identified at least to their genus designation by means of conventional biochemistry and morphological indicators. Furthermore, the biochemical assays for confirmed Gram-negative strains such as *Paracoccus kondratievae, Alcaligenes faecalis*, and *Enterobacter cloacae* included growth on MacConkey medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; starch hydrolysis; oxidase reaction, catalase production, urease production and motility. Similarly, the biochemical assays for confirmed Gram-positive strains such as *Bacillus* and *Paenibacillus* included growth in phenylethyl alcohol (PEA) medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility.

The present invention also relates to a biologically pure bacterial culture wherein bacteria, i.e. the bacterial strain in the bacterial culture, are mutants of any of the foregoing bacterial strains, which comprises one or more mutations that retain the ability to promote plant growth. Thus, the mutant of any of the foregoing strains will be capable of promoting plant growth when compared to plants to which the mutant was not applied. For example, the mutant can comprise a salt-tolerant mutant (e.g., salt-tolerant mutant of *Paracoccus kondratievae* strain NC35 or a salt-tolerant mutant of *Bacillus mycoides* strain BT155), a thiram-resistant mutant (e.g., a thiram-resistant mutant of *Paracoccus kondratievae* strain NC35, a thiram-resistant mutant of *Bacillus aryabhatti* strain CAP53, a thiram-resistant mutant of *Bacillus mycoides* strain BT155, or a thiram-resistant mutant of *Bacillus thuringiensis* BT013A), or a glyphosate-tolerant mutant (e.g., a glyphosate-tolerant mutant of *Bacillus aryabhatti* strain CAP53).

The following assays can be used, either individually or in concert, to identify mutant strains, which are capable under gnotobiotic conditions to increase leaf area in 3- to 4-week old whole plants (beaker assay), to increase shoot length or shoot dry weight (soil-plate assay), or to increase root length, root dry weight, shoot dry weight and shoot length (growth pouch assay), which are positively correlated with the ability to promote growth directly in whole plants grown in raw (nonsterilized) soil. In a "Beaker Assay," a mixture of field soil and perlite is sterilized, e.g., by gamma-irradiation (about 1 mRad has proved suitable). Samples of the mix are transferred aseptically to sterile, covered beakers, to which enough water or nutrient solution is added to achieve a moisture content of roughly 25%. Surface-sterilized seed of a test plant, such as rape (*Brassica napus* and *Brassica campestris*), radish, wheat, soybean, corn or cotton, are then sown (1 seed per beaker) after briefly incubating in an aqueous bacterial cell suspension of the strain under study. (A bacterial concentration in the range of $10^9$ colony forming units (CFU) per ml of suspension has proved suitable for this purpose.) After seedlings have developed, under controlled conditions suitable to the test plant, to a point where mature leaves have grown, those plants subjected to bacterial treatments are compared against uninoculated controls to ascertain differences in leaf area between test and control groups.

In a "Soil-plate Assay," Petri plates are filled with ground, air-dried soil that has been sterilized by autoclaving, gamma-irradiation, etc. The soil in each plate is then moistened and left covered overnight to assure a uniform moisture distribution through the soil. Inoculated (test) and control seeds, as described above, are thereafter sown in each plate, some six to eight seeds per plate at about 1 cm depth, and grown in the dark under appropriate conditions of temperature and humidity until shoots develop. At the end of incubation, the shoot lengths are determined. In a "Growth Pouch Assay," cellophane containers of the type heretofore used as seed-pack growth pouches are filled with a small volume of deionized water or mineral solution and autoclaved to assure sterility. Test seeds incubated in a bacterial suspension, as previously described, and control seeds not exposed to the bacteria are aseptically sown, about six seeds to a pouch, respectively, and are germinated in the dark under suitable, controlled conditions. After shoots have developed, the pouches are opened and the seedling root length, root dry weight, shoot length and shoot dry weight determined for both tests and controls. Alternatively, the mutant strains can be tested as shown in the Examples for any of the foregoing bacterial strains with respect to the ability to promote plant growth.

The present invention is also directed to an inoculum for application to plants, plant seeds, or a plant growth medium, wherein the inoculum comprises an effective amount of a biologically pure bacterial culture of *Bacillus aryabhattai* strain CAP53 (NRRL No. B-50819), *Bacillus aryabhattai* strain CAP56 (NRRL No. B-50817), *Bacillus flexus* strain BT054 (NRRL No. B-50816), *Paracoccus kondratievae* strain NC35 (NRRL No. B-50820), *Bacillus mycoides* strain BT155 (NRRL No. B-50921), *Enterobacter cloacae* strain CAP12 (NRRL No. B-50822), *Bacillus nealsonii* strain BOBA57 (NRRL No. B-50821), *Bacillus mycoides* strain EE118 (NRRL No. B-50918), *Bacillus subtilis* strain EE148 (NRRL No. B-50927), *Alcaligenes faecalis* strain EE107 (NRRL No. B-50920), *Bacillus mycoides* strain EE141 (NRRL No. B-50916), *Bacillus mycoides* strain BT46-3 (NRRL No. B-50922), *Bacillus cereus* family member strain EE128 (NRRL No. B-50917), *Bacillus thuringiensis* strain BT013A (NRRL No. B-50924), *Paenibacillus massiliensis* strain BT23 (NRRL No. B-50923), *Bacillus cereus* strain family member EE349 (NRRL No. B-50928), *Bacillus subtilis* strain EE218 (NRRL No. B-50926), *Bacillus megaterium* strain EE281 (NRRL No. B-50925) or a mutant of any of the foregoing strains, and an agriculturally acceptable carrier. Alternatively, the inoculum of the present invention can include an effective amount of a mixture comprising at least two biologically pure bacterial cultures described herein. Thus, the mixture of two biologically pure bacterial cultures can include *Bacillus aryabhattai* strain CAP53 and *Bacillus aryabhattai* strain CAP56; *Bacillus aryabhattai* strain CAP53 and *Bacillus flexus* strain BT054; *Bacillus aryabhattai* strain CAP53 and *Paracoccus kondratievae* strain NC35; *Bacillus aryabhattai* strain CAP53 and *Bacillus mycoides* strain BT155; *Bacillus aryabhattai* strain CAP53 and *Enterobacter cloacae* strain CAP12; *Bacillus aryabhattai* strain CAP53 and *Bacillus nealsonii* strain BOBA57; *Bacillus aryabhattai* strain CAP53 and *Bacillus mycoides* strain EE118; *Bacillus aryabhattai* strain CAP53 and *Bacillus subtilis* strain EE148; *Bacillus aryabhattai* strain CAP53 and *Alcaligenes faecalis* strain EE107; *Bacillus aryabhattai* strain CAP53 and *Bacillus mycoides* strain EE141; *Bacillus aryabhattai* strain CAP53 and *Bacillus mycoides* strain BT46-3; *Bacillus aryabhattai* strain CAP53 and *Bacillus cereus* family member strain EE128; *Bacillus aryabhattai* strain CAP53 and *Bacillus thuringiensis* strain BT013A; *Bacillus aryabhattai* strain CAP53 and *Paenibacillus massiliensis* strain BT23; *Bacillus aryabhattai* strain CAP53 and *Bacillus cereus* family member strain EE349; *Bacillus aryabhattai* strain CAP53 and *Bacillus subtilis* strain EE218; *Bacillus aryabhattai* strain CAP53 and *Bacillus megaterium* strain EE281; *Bacillus aryabhattai* strain CAP53 and salt-tolerant and thiram-resistant *Paracoccus* sp. NC35; *Bacillus aryabhattai* strain CAP53 and salt-tolerant and thiram-resistant *Bacillus mycoides* strain BT155; *Bacillus aryabhattai* strain CAP53 and thiram-resistant *Bacillus aryabhattai* CAP53; *Bacillus aryabhattai* strain CAP53 and thiram-resistant *Bacillus thuringiensis* BT013A; *Bacillus aryabhattai* strain CAP53 and glyphosate-tolerant *Bacillus aryabhattai* CAP53; *Bacillus aryabhattai* strain CAP56 and *Bacillus flexus* strain BT054; *Bacillus aryabhattai* strain CAP56 and *Paracoccus kondratievae* strain NC35; *Bacillus aryabhattai* strain CAP56 and *Bacillus mycoides* strain BT155; *Bacillus aryabhattai* strain CAP56 and *Enterobacter cloacae* strain CAP12; *Bacillus aryabhattai* strain CAP56 and *Bacillus nealsonii* strain BOBA57; *Bacillus aryabhattai* strain CAP56 and *Bacillus mycoides* strain EE118; *Bacillus aryabhattai* strain CAP56 and *Bacillus subtilis* strain EE148; *Bacillus aryabhattai* strain CAP56 and *Alcaligenes faecalis* strain EE107; *Bacillus aryabhattai* strain CAP56 and *Bacillus mycoides* strain EE141; *Bacillus aryabhattai* strain CAP56 and *Bacillus mycoides* strain BT46-3; *Bacillus aryabhattai* strain CAP56 and *Bacillus cereus* family member strain EE128; *Bacillus aryabhattai* strain CAP56 and *Bacillus thuringiensis* strain BT013A; *Bacillus aryabhattai* strain CAP56 and *Paenibacillus massiliensis* strain BT23; *Bacillus aryabhattai* strain CAP56 and *Bacillus cereus* family member strain EE349; *Bacillus aryabhattai* strain CAP56 and *Bacillus subtilis* strain EE218; *Bacillus aryabhattai* strain CAP56 and *Bacillus megaterium* strain EE281; *Bacillus aryabhattai* strain CAP56 and salt-tolerant and thiram-resistant *Paracoccus* sp. NC35; *Bacillus aryabhattai* strain CAP56 and salt-tolerant and thiram-resistant *Bacillus mycoides* strain BT155; *Bacillus aryabhattai* strain CAP56 and thiram-resistant *Bacillus aryabhattai* CAP53; *Bacillus aryabhattai* strain CAP56 and thiram-resistant *Bacillus thuringiensis* BT013A; *Bacillus aryabhattai* strain CAP56 and glyphosate-tolerant *Bacillus aryabhattai* CAP53; *Bacillus flexus* strain BT054 and *Paracoccus kondratievae* strain NC35; *Bacillus flexus* strain BT054 and *Bacillus mycoides* strain BT155; *Bacillus flexus* strain BT054 and *Enterobacter cloacae* strain CAP12; *Bacillus flexus* strain BT054 and *Bacillus nealsonii* strain BOBA57; *Bacillus flexus* strain BT054 and *Bacillus mycoides* strain EE118; *Bacillus flexus* strain BT054 and *Bacillus subtilis* strain EE148; *Bacillus flexus* strain BT054 and *Alcaligenes faecalis* strain EE107; *Bacillus flexus* strain BT054 and *Bacillus mycoides* strain EE141; *Bacillus flexus* strain BT054 and *Bacillus mycoides* strain BT46-3; *Bacillus flexus* strain BT054 and *Bacillus cereus* family member strain EE128; *Bacillus flexus* strain BT054 and *Bacillus thuringiensis* strain BT013A; *Bacillus flexus* strain BT054 and *Paenibacillus massiliensis* strain BT23; *Bacillus flexus* strain BT054 and *Bacillus cereus* family member strain EE349; *Bacillus flexus* strain BT054 and *Bacillus subtilis* strain EE218; *Bacillus flexus* strain BT054 and *Bacillus megaterium* strain EE281; *Bacillus flexus* strain BT054 and salt-tolerant and thiram-resistant *Paracoccus* sp. NC35; *Bacillus flexus* strain BT054 and salt-tolerant and thiram-resistant *Bacillus mycoides* strain BT155; *Bacillus flexus* strain BT054 and thiram-resistant *Bacillus aryabhattai* CAP53; *Bacillus flexus* strain BT054 and thiram-resistant *Bacillus thuringiensis* BT013A; *Bacillus flexus* strain BT054 and glyphosate-tolerant *Bacillus aryabhattai* CAP53; *Paracoccus kondratievae* strain NC35 and *Bacillus mycoides* strain BT155; *Paracoccus kondratievae* strain NC35 and *Enterobacter cloacae* strain CAP12; *Paracoccus kondratievae* strain NC35 and *Bacillus nealsonii* strain BOBA57; *Paracoccus kondratievae* strain NC35 and *Bacillus mycoides* strain EE118; *Paracoccus kondratievae* strain NC35 and *Bacillus subtilis* strain EE148; *Paracoccus kondratievae* strain NC35 and *Alcaligenes faecalis* strain EE107; *Paracoccus kondratievae* strain NC35 and *Bacillus mycoides* strain EE141; *Paracoccus kondratievae* strain NC35 and *Bacillus mycoides* strain BT46-3; *Paracoccus kondratievae* strain NC35 and *Bacillus cereus* family member strain EE128; *Paracoccus kondratievae* strain NC35 and *Bacillus thuringiensis* strain BT013A; *Paracoccus kondratievae* strain NC35 and *Paenibacillus massiliensis* strain BT23; *Paracoccus kondratievae* strain NC35 and *Bacillus cereus* family member strain EE349; *Paracoccus kondratievae* strain NC35 and *Bacillus subtilis* strain EE218; *Paracoccus kondratievae* strain NC35 and *Bacillus megaterium* strain EE281; *Paracoccus kondratievae* strain NC35 and salt-tolerant and thiram-resistant *Paracoccus* sp. NC35; *Paracoccus kondratievae* strain NC35 and salt-tolerant and thiram-resistant *Bacillus mycoides* strain BT155; *Paracoccus kondratievae* strain NC35 and thiram-resistant *Bacillus*

*aryabhattai* CAP53; *Paracoccus kondratievae* strain NC35 and thiram-resistant *Bacillus thuringiensis* BT013A; *Paracoccus kondratievae* strain NC35 and glyphosate-tolerant *Bacillus aryabhattai* CAP53; *Bacillus mycoides* strain BT155 and *Enterobacter cloacae* strain CAP12; *Bacillus mycoides* strain BT155 and *Bacillus nealsonii* strain BOBA57; *Bacillus mycoides* strain BT155 and *Bacillus mycoides* strain EE118; *Bacillus mycoides* strain BT155 and *Bacillus subtilis* strain EE148; *Bacillus mycoides* strain BT155 and *Alcaligenes faecalis* strain EE107; *Bacillus mycoides* strain BT155 and *Bacillus mycoides* strain EE141; *Bacillus mycoides* strain BT155 and *Bacillus mycoides* strain BT46-3; *Bacillus mycoides* strain BT155 and *Bacillus cereus* family member strain EE128; *Bacillus mycoides* strain BT155 and *Bacillus thuringiensis* strain BT013A; *Bacillus mycoides* strain BT155 and *Paenibacillus massiliensis* strain BT23; *Bacillus mycoides* strain BT155 and *Bacillus cereus* family member strain EE349; *Bacillus mycoides* strain BT155 and *Bacillus subtilis* strain EE218; *Bacillus mycoides* strain BT155 and *Bacillus megaterium* strain EE281; *Bacillus mycoides* strain BT155 and salt-tolerant and thiram-resistant *Paracoccus* sp. NC35; *Bacillus mycoides* strain BT155 and salt-tolerant and thiram-resistant *Bacillus mycoides* strain BT155; *Bacillus mycoides* strain BT155 and thiram-resistant *Bacillus aryabhattai* CAP53; *Bacillus mycoides* strain BT155 and thiram-resistant *Bacillus thuringiensis* BT013A; *Bacillus mycoides* strain BT155 and glyphosate-tolerant *Bacillus aryabhattai* CAP53; *Enterobacter cloacae* strain CAP12 and *Bacillus nealsonii* strain BOBA57; *Enterobacter cloacae* strain CAP12 and *Bacillus mycoides* strain EE118; *Enterobacter cloacae* strain CAP12 and *Bacillus subtilis* strain EE148; *Enterobacter cloacae* strain CAP12 and *Alcaligenes faecalis* strain EE107; *Enterobacter cloacae* strain CAP12 and *Bacillus mycoides* strain EE141; *Enterobacter cloacae* strain CAP12 and *Bacillus mycoides* strain BT46-3; *Enterobacter cloacae* strain CAP12 and *Bacillus cereus* family member strain EE128; *Enterobacter cloacae* strain CAP12 and *Bacillus thuringiensis* strain BT013A; *Enterobacter cloacae* strain CAP12 and *Paenibacillus massiliensis* strain BT23; *Enterobacter cloacae* strain CAP12 and *Bacillus cereus* family member strain EE349; *Enterobacter cloacae* strain CAP12 and *Bacillus subtilis* strain EE218; *Enterobacter cloacae* strain CAP12 and *Bacillus megaterium* strain EE281; *Enterobacter cloacae* strain CAP12 and salt-tolerant and thiram-resistant *Paracoccus* sp. NC35; *Enterobacter cloacae* strain CAP12 and salt-tolerant and thiram-resistant *Bacillus mycoides* strain BT155; *Enterobacter cloacae* strain CAP12 and thiram-resistant *Bacillus aryabhattai* CAP53; *Enterobacter cloacae* strain CAP12 and thiram-resistant *Bacillus thuringiensis* BT013A; *Enterobacter cloacae* strain CAP12 and glyphosate-tolerant *Bacillus aryabhattai* CAP53; *Bacillus nealsonii* strain BOBA57 and *Bacillus mycoides* strain EE118; *Bacillus nealsonii* strain BOBA57 and *Bacillus subtilis* strain EE148; *Bacillus nealsonii* strain BOBA57 and *Alcaligenes faecalis* strain EE107; *Bacillus nealsonii* strain BOBA57 and *Bacillus mycoides* strain EE141; *Bacillus nealsonii* strain BOBA57 and *Bacillus mycoides* strain BT46-3; *Bacillus nealsonii* strain BOBA57 and *Bacillus cereus* family member strain EE128; *Bacillus nealsonii* strain BOBA57 and *Bacillus thuringiensis* strain BT013A; *Bacillus nealsonii* strain BOBA57 and *Paenibacillus massiliensis* strain BT23; *Bacillus nealsonii* strain BOBA57 and *Bacillus cereus* family member strain EE349; *Bacillus nealsonii* strain BOBA57 and *Bacillus subtilis* strain EE218; *Bacillus nealsonii* strain BOBA57 and *Bacillus megaterium* strain EE281; *Bacillus nealsonii* strain BOBA57 and salt-tolerant and thiram-resistant *Paracoccus* sp. NC35; *Bacillus nealsonii* strain BOBA57 and salt-tolerant and thiram-resistant *Bacillus mycoides* strain BT155; *Bacillus nealsonii* strain BOBA57 and thiram-resistant *Bacillus aryabhattai* CAP53; *Bacillus nealsonii* strain BOBA57 and thiram-resistant *Bacillus thuringiensis* BT013A; *Bacillus nealsonii* strain BOBA57 and glyphosate-tolerant *Bacillus aryabhattai* CAP53; *Bacillus mycoides* strain EE118 and *Bacillus subtilis* strain EE148; *Bacillus mycoides* strain EE118 and *Alcaligenes faecalis* strain EE107; *Bacillus mycoides* strain EE118 and *Bacillus mycoides* strain EE141; *Bacillus mycoides* strain EE118 and *Bacillus mycoides* strain BT46-3; *Bacillus mycoides* strain EE118 and *Bacillus cereus* family member strain EE128; *Bacillus mycoides* strain EE118 and *Bacillus thuringiensis* strain BT013A; *Bacillus mycoides* strain EE118 and *Paenibacillus massiliensis* strain BT23; *Bacillus mycoides* strain EE118 and *Bacillus cereus* family member strain EE349; *Bacillus mycoides* strain EE118 and *Bacillus subtilis* strain EE218; *Bacillus mycoides* strain EE118 and *Bacillus megaterium* strain EE281; *Bacillus mycoides* strain EE118 and salt-tolerant and thiram-resistant *Paracoccus* sp. NC35; *Bacillus mycoides* strain EE118 and salt-tolerant and thiram-resistant *Bacillus mycoides* strain BT155; *Bacillus mycoides* strain EE118 and thiram-resistant *Bacillus aryabhattai* CAP53; *Bacillus mycoides* strain EE118 and thiram-resistant *Bacillus thuringiensis* BT013A; *Bacillus mycoides* strain EE118 and glyphosate-tolerant *Bacillus aryabhattai* CAP53; *Bacillus subtilis* strain EE148 and *Alcaligenes faecalis* strain EE107; *Bacillus subtilis* strain EE148 and *Bacillus mycoides* strain EE141; *Bacillus subtilis* strain EE148 and *Bacillus mycoides* strain BT46-3; *Bacillus subtilis* strain EE148 and *Bacillus cereus* family member strain EE128; *Bacillus subtilis* strain EE148 and *Bacillus thuringiensis* strain BT013A; *Bacillus subtilis* strain EE148 and *Paenibacillus massiliensis* strain BT23; *Bacillus subtilis* strain EE148 and *Bacillus cereus* family member strain EE349; *Bacillus subtilis* strain EE148 and *Bacillus subtilis* strain EE218; *Bacillus subtilis* strain EE148 and *Bacillus megaterium* strain EE281; *Bacillus subtilis* strain EE148 and salt-tolerant and thiram-resistant *Paracoccus* sp. NC35; *Bacillus subtilis* strain EE148 and salt-tolerant and thiram-resistant *Bacillus mycoides* strain BT155; *Bacillus subtilis* strain EE148 and thiram-resistant *Bacillus aryabhattai* CAP53; *Bacillus subtilis* strain EE148 and thiram-resistant *Bacillus thuringiensis* BT013A; *Bacillus subtilis* strain EE148 and glyphosate-tolerant *Bacillus aryabhattai* CAP53; *Alcaligenes faecalis* strain EE107 and *Bacillus mycoides* strain EE141; *Alcaligenes faecalis* strain EE107 and *Bacillus mycoides* strain BT46-3; *Alcaligenes faecalis* strain EE107 and *Bacillus cereus* family member strain EE128; *Alcaligenes faecalis* strain EE107 and *Bacillus thuringiensis* strain BT013A; *Alcaligenes faecalis* strain EE107 and *Paenibacillus massiliensis* strain BT23; *Alcaligenes faecalis* strain EE107 and *Bacillus cereus* family member strain EE349; *Alcaligenes faecalis* strain EE107 and *Bacillus subtilis* strain EE218; *Alcaligenes faecalis* strain EE107 and *Bacillus megaterium* strain EE281; *Alcaligenes faecalis* strain EE107 and salt-tolerant and thiram-resistant *Paracoccus* sp. NC35; *Alcaligenes faecalis* strain EE107 and salt-tolerant and thiram-resistant *Bacillus mycoides* strain BT155; *Alcaligenes faecalis* strain EE107 and thiram-resistant *Bacillus aryabhattai* CAP53; *Alcaligenes faecalis* strain EE107 and thiram-resistant *Bacillus thuringiensis* BT013A; *Alcaligenes faecalis* strain EE107 and glyphosate-tolerant *Bacillus aryabhattai* CAP53; *Bacillus mycoides* strain EE141 and *Bacillus mycoides* strain BT46-3; *Bacillus mycoides* strain EE141 and *Bacillus cereus* family member strain EE128; *Bacillus mycoides* strain EE141 and *Bacillus thuringiensis* strain BT013A; *Bacillus mycoides* strain EE141 and *Paenibacillus massiliensis* strain BT23; *Bacillus mycoides* strain EE141 and *Bacillus cereus* family member strain EE349; *Bacillus mycoides* strain EE141 and *Bacillus subtilis* strain EE218; *Bacillus mycoides* strain EE141 and *Bacillus megaterium* strain EE281; *Bacillus mycoides* strain EE141 and salt-tolerant and thiram-resistant *Paracoccus* sp. NC35; *Bacillus mycoides* strain EE141 and salt-tolerant and thiram-resistant *Bacillus mycoides* strain BT155; *Bacillus mycoides* strain EE141 and thiram-resistant *Bacillus aryabhattai* CAP53; *Bacillus mycoides* strain EE141 and thiram-resistant *Bacillus thuringiensis* BT013A; *Bacillus mycoides* strain EE141 and glyphosate-tolerant *Bacillus aryabhattai* CAP53; *Bacillus mycoides* strain BT46-3 and *Bacillus cereus* family member strain EE128; *Bacillus mycoides* strain BT46-3 and *Bacillus thuringiensis* strain BT013A; *Bacillus mycoides* strain BT46-3 and *Paenibacillus massiliensis* strain BT23; *Bacillus mycoides* strain BT46-3 and *Bacillus cereus* family member strain EE349; *Bacillus mycoides* strain BT46-3 and *Bacillus subtilis* strain EE218; *Bacillus mycoides* strain BT46-3 and *Bacillus megaterium* strain EE281; *Bacillus mycoides* strain BT46-3 and salt-tolerant and thiram-resistant *Paracoccus* sp. NC35; *Bacillus mycoides* strain BT46-3 and salt-tolerant and thiram-resistant *Bacillus mycoides* strain BT155; *Bacillus mycoides* strain BT46-3 and thiram-resistant *Bacillus aryabhattai* CAP53; *Bacillus mycoides* strain BT46-3 and thiram-resistant *Bacillus thuringiensis* BT013A; *Bacillus mycoides* strain BT46-3 and glyphosate-tolerant *Bacillus aryabhattai* CAP53; *Bacillus cereus* family member strain EE128 and *Bacillus thuringiensis* strain BT013A; *Bacillus cereus* family member strain EE128 and *Paenibacillus massiliensis* strain BT23; *Bacillus cereus* family member strain EE128 and *Bacillus cereus* family member strain EE349; *Bacillus cereus* family member strain EE128 and *Bacillus subtilis* strain EE218; *Bacillus cereus* family member strain EE128 and *Bacillus megaterium* strain EE281; *Bacillus cereus* family member strain EE128 and salt-tolerant and thiram-resistant *Paracoccus* sp. NC35; *Bacillus cereus* family member strain EE128 and salt-tolerant and thiram-resistant *Bacillus mycoides* strain BT155; *Bacillus cereus* family member strain EE128 and thiram-resistant *Bacillus aryabhattai* CAP53; *Bacillus cereus* family member strain EE128 and thiram-resistant *Bacillus thuringiensis* BT013A; *Bacillus cereus* family member strain EE128 and glyphosate-tolerant *Bacillus aryabhattai* CAP53; *Bacillus thuringiensis* strain BT013A and *Paenibacillus massiliensis* strain BT23; *Bacillus thuringiensis* strain BT013A and *Bacillus cereus* family member strain EE349; *Bacillus thuringiensis* strain BT013A and *Bacillus subtilis* strain EE218; *Bacillus thuringiensis* strain BT013A and *Bacillus megaterium* strain EE281; *Bacillus thuringiensis* strain BT013A and salt-tolerant and thiram-resistant *Paracoccus* sp. NC35; *Bacillus thuringiensis* strain BT013A and salt-tolerant and thiram-resistant *Bacillus mycoides* strain BT155; *Bacillus thuringiensis* strain BT013A and thiram-resistant *Bacillus aryabhattai* CAP53; *Bacillus thuringiensis* strain BT013A and thiram-resistant *Bacillus thuringiensis* BT013A; *Bacillus thuringiensis* strain BT013A and glyphosate-tolerant *Bacillus aryabhattai* CAP53; *Paenibacillus massiliensis* strain BT23 and *Bacillus cereus* family member strain EE349; *Paenibacillus massiliensis* strain BT23 and *Bacillus subtilis* strain EE218; *Paenibacillus massiliensis* strain BT23 and *Bacillus megaterium* strain EE281; *Paenibacillus massiliensis* strain BT23 and salt-tolerant and thiram-resistant *Paracoccus* sp. NC35; *Paenibacillus massiliensis* strain BT23 and salt-tolerant and thiram-resistant *Bacillus mycoides* strain BT155; *Paenibacillus massiliensis* strain BT23 and thiram-resistant *Bacillus aryabhattai* CAP53; *Paenibacillus massiliensis* strain BT23 and thiram-resistant *Bacillus thuringiensis* BT013A; *Paenibacillus massiliensis* strain BT23 and glyphosate-tolerant *Bacillus aryabhattai* CAP53; *Bacillus cereus* family member strain EE349 and *Bacillus subtilis* strain EE218; *Bacillus cereus* family member strain EE349 and *Bacillus megaterium* strain EE281; *Bacillus cereus* family member strain EE349 and salt-tolerant and thiram-resistant *Paracoccus* sp. NC35; *Bacillus cereus* family member strain EE349 and salt-tolerant and thiram-resistant *Bacillus mycoides* strain BT155; *Bacillus cereus* family member strain EE349 and thiram-resistant *Bacillus aryabhattai* CAP53; *Bacillus cereus* family member strain EE349 and thiram-resistant *Bacillus thuringiensis* BT013A; *Bacillus cereus* family member strain EE349 and glyphosate-tolerant *Bacillus aryabhattai* CAP53; *Bacillus subtilis* strain EE218 and *Bacillus megaterium* strain EE281; *Bacillus subtilis* strain EE218 and salt-tolerant and thiram-resistant *Paracoccus* sp. NC35; *Bacillus subtilis* strain EE218 and salt-tolerant and thiram-resistant *Bacillus mycoides* strain BT155; *Bacillus subtilis* strain EE218 and thiram-resistant *Bacillus aryabhattai* CAP53; *Bacillus subtilis* strain EE218 and thiram-resistant *Bacillus thuringiensis* BT013A; *Bacillus subtilis* strain EE218 and glyphosate-tolerant *Bacillus aryabhattai* CAP53; *Bacillus megaterium* strain EE281 and salt-tolerant and thiram-resistant *Paracoccus* sp. NC35; *Bacillus megaterium* strain EE281 and salt-tolerant and thiram-resistant *Bacillus mycoides* strain BT155; *Bacillus megaterium* strain EE281 and thiram-resistant *Bacillus aryabhattai* CAP53; *Bacillus megaterium* strain EE281 and thiram-resistant *Bacillus thuringiensis* BT013A; or *Bacillus megaterium* strain EE281 and glyphosate-tolerant *Bacillus aryabhattai* CAP53.

An inoculum which includes an effective amount of a mixture of three bacteriologically pure bacterial cultures can include *Bacillus aryabhattai* strain CAP53, *Bacillus aryabhattai* strain CAP56, and *Bacillus flexus* strain BT054; *Bacillus aryabhattai* strain CAP53, *Bacillus aryabhattai* strain CAP56, and *Paracoccus kondratievae* strain NC35; *Bacillus aryabhattai* strain CAP53, *Bacillus aryabhattai* strain CAP56, and *Bacillus mycoides* strain BT155; *Bacillus aryabhattai* strain CAP53, *Bacillus aryabhattai* strain CAP56, and *Enterobacter cloacae* strain CAP12; *Bacillus aryabhattai* strain CAP53, *Bacillus aryabhattai* strain CAP56, and *Bacillus nealsonii* strain BOBA57; *Bacillus aryabhattai* strain CAP53, *Bacillus flexus* strain BT054, and *Paracoccus kondratievae* strain NC35; *Bacillus aryabhattai* strain CAP53, *Bacillus flexus* strain BT054, and *Bacillus mycoides* strain BT155; *Bacillus aryabhattai* strain CAP53, *Bacillus flexus* strain BT054, and *Enterobacter cloacae* strain CAP12; *Bacillus aryabhattai* strain CAP53, *Bacillus flexus* strain BT054, and *Bacillus nealsonii* strain BOBA57; *Bacillus aryabhattai* strain CAP53, *Paracoccus kondratievae* strain NC35, and *Bacillus mycoides* strain BT155; *Bacillus aryabhattai* strain CAP53, *Paracoccus kondratievae* strain NC35, and *Enterobacter cloacae* strain CAP12; *Bacillus aryabhattai* strain CAP53, *Paracoccus kondratievae* strain NC35, and *Bacillus nealsonii* strain BOBA57; *Bacillus aryabhattai* strain CAP53, *Bacillus mycoides* strain BT155, and *Enterobacter cloacae* strain CAP12; *Bacillus aryabhattai* strain CAP53, *Bacillus mycoides* strain BT155, and *Bacillus nealsonii* strain BOBA57; *Bacillus aryabhattai* strain CAP56, *Bacillus flexus* strain BT054, and *Paracoccus*

*kondratievae* strain NC35; *Bacillus aryabhattai* strain CAP56, *Bacillus flexus* strain BT054, and *Bacillus mycoides* strain BT155; *Bacillus aryabhattai* strain CAP56, *Bacillus flexus* strain BT054, and *Enterobacter cloacae* strain CAP12; *Bacillus aryabhattai* strain CAP56, *Bacillus flexus* strain BT054, and *Bacillus nealsonii* strain BOBA57; *Bacillus aryabhattai* strain CAP56, *Paracoccus kondratievae* strain NC35, and *Bacillus mycoides* strain BT155; *Bacillus aryabhattai* strain CAP56, *Paracoccus kondratievae* strain NC35, and *Enterobacter cloacae* strain CAP12; *Bacillus aryabhattai* strain CAP56, *Paracoccus kondratievae* strain NC35, and *Bacillus nealsonii* strain BOBA57; *Bacillus aryabhattai* strain CAP56, *Bacillus mycoides* strain BT155, and *Enterobacter cloacae* strain CAP12; *Bacillus aryabhattai* strain CAP56, *Bacillus mycoides* strain BT155, and *Bacillus nealsonii* strain BOBA57; *Bacillus aryabhattai* strain CAP56, *Enterobacter cloacae* strain CAP12, and *Bacillus nealsonii* strain BOBA57; *Bacillus flexus* strain BT054, *Paracoccus kondratievae* strain NC35, and *Bacillus mycoides* strain BT155; *Bacillus flexus* strain BT054, *Paracoccus kondratievae* strain NC35, and *Enterobacter cloacae* strain CAP12; *Bacillus flexus* strain BT054, *Paracoccus kondratievae* strain NC35, and *Bacillus nealsonii* strain BOBA57; *Bacillus flexus* strain BT054, *Bacillus mycoides* strain BT155, and *Enterobacter cloacae* strain CAP12; *Bacillus flexus* strain BT054, *Bacillus mycoides* strain BT155, and *Bacillus nealsonii* strain BOBA57; *Bacillus flexus* strain BT054, *Enterobacter cloacae* strain CAP12, and *Bacillus nealsonii* strain BOBA57; *Paracoccus kondratievae* strain NC35, *Bacillus mycoides* strain BT155, and *Enterobacter cloacae* strain CAP12; *Paracoccus kondratievae* strain NC35, *Bacillus mycoides* strain BT155, and *Bacillus nealsonii* strain BOBA57; *Paracoccus kondratievae* strain NC35, *Enterobacter cloacae* strain CAP12, and *Bacillus nealsonii* strain BOBA57; or *Bacillus mycoides* strain BT155, *Enterobacter cloacae* strain CAP12, and *Bacillus nealsonii* strain BOBA57.

The following mixtures of bacteriologically pure bacterial cultures are favorable for use in stimulating plant growth. They include, without limitation, mixtures of: (1) *Enterobacter cloacae* CAP12 and *Bacillus aryabhattai* CAP53; (2) *Enterobacter cloacae* CAP12 and *Bacillus aryabhattai* CAP56; (3) *Enterobacter cloacae* CAP12 and *Bacillus flexus* BT054; (4) *Enterobacter cloacae* CAP12 and *Bacillus nealsonii* BOBA57; (5) *Bacillus aryabhattai* CAP53 and *Bacillus aryabhattai* CAP56; (6) *Bacillus flexus* BT054 and *Bacillus aryabhattai* CAP56, (7) *Paracoccus kondratievae* NC35 and *Bacillus mycoides* BT155, (8) *Bacillus subtilis* EE218 and *Paracoccus kondratievae* NC35, and (9) *Bacillus subtilis* EE218 and *Bacillus mycoides* BT155.

Rhizobacteria are root-colonizing bacteria that form symbiotic relationships with many plants, and as such are useful in promoting plant growth. Accordingly, any of the inoculums of the present invention regardless of whether they contains a single bacterial strain disclosed herein or a mixture of two or more such bacterial strains can also include an effective amount of rhizobacteria.

Such rhizobacteria can be present as a biologically pure bacterial culture. Alternatively, rhizobacteria that are used in the inoculums of the present invention can include two or more strains of rhizobacteria. By way of example and not of limitation, the rhizobacteria can include *Bradyrhizobium* genus bacteria, *Rhizobium* genus bacteria, or a combination thereof. Also, the *Bradirhizobium* genus bacteria can comprise *Bradyrhizobium japonicum*, and the *Rhizobium* genus bacteria can comprise *Rhizobium phaseoli*, *Rhizobium leguminosarum*, or a combination thereof. The inclusion of rhizobacteria in the present compositions and methods is especially advantageous in so-called "virgin soils" which do not contain an indigenous population of PGPB such as nitrogen fixing rhizobia. This may occur e.g. where nitrogen-fixing legume crops have not been previously or recently grown.

In addition to one or more biologically pure bacterial cultures as described in the foregoing sections, an inoculum of the present invention also comprises an agriculturally acceptable carrier. The carrier can include a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof. One of ordinary skill in the art can readily determine the appropriate carrier to be used taking into consideration factors such as a particular bacterial strain, plant to which the inoculum is to be applied, type of soil, climate conditions, whether the inoculum is in liquid, solid or powder form, and the like.

The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutant dioate, a benzene acetonitrile derivative, a proteinaceous material, or a combination thereof.

The proteinaceous material can include a milk product, wheat flour, soybean meal, alfalfa meal, yeast extract, blood, albumin, gelatin, or a combination thereof.

The thickener can comprise a long chain alkylsulfonate of polyethylene glycol, polyoxyethylene oleate, or a combination thereof.

The surfactant can contain a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof.

The anti-caking agent can include a sodium salt such as a sodium sulfite, a sodium sulfate, a sodium salt of monomethyl naphthalene sulfonate, a sodium salt of dimethyl naphthalene sulfonate, or a combination thereof; or a calcium salt such as calcium carbonate, diatomaceous earth, or a combination thereof.

Any agriculturally acceptable carrier can be used. Such carriers include, but are not limited to, vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

Inoculants can be prepared as solid, liquid or powdered formulations as is known in the art. The inoculum of the present invention can be formulated as a seed coating formulation, a liquid formulation for application to plants or to a plant growth medium, or a solid formulation for application to plants or to a plant growth medium.

When the inoculum is prepared as a liquid formulation for application to plants or to a plant growth medium, it can be prepared in a concentrated formulation or a ready-to-use formulation. In some instances, the seed coating formulation of the present invention is an aqueous or oil-based solution for application to seeds.

When the inoculum of the present invention is prepared as a solid formulation for application to plants or to a plant growth medium, it can be prepared as a granular formulation or a powder agent. The seed coating formulation can be a powder or granular formulation for application to seeds.

The inoculum can further include an agrochemical such as a fertilizer, a micronutrient fertilizer material, an insecticide, a herbicide, a plant growth amendment, a fungicide, a molluscicide, an algicide, a bacterial inoculant, a fungal inoculant, or a combination thereof. In some instances, the fertilizer is a liquid fertilizer. The agrochemical can either be applied to a plant growth medium or to plants and/or seeds. Liquid fertilizer can include, without limitation, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, or a combination thereof.

The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The insecticide can include an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivative, oxadiazolinone, a phosphate, a phthalate, a picolinic acid compound, a triazine, a triazole, a uracil, a urea derivative, endothall, sodium chlorate, or a combination thereof.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

The fungal inoculant can comprise a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof.

The bacterial inoculant, for purposes of the present invention, can include a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

All of the biologically pure bacterial cultures and inoculums of the present invention can be used in methods for stimulating plant growth. Such methods include applying the foregoing cultures and inoculums to a plant, plant seed, or plant growth medium in order to stimulate growth of the plant. Techniques for applying inoculants to plants are known in the art, including appropriate modes of administration, frequency of administration, dosages, and the like. The inoculant can be applied to the soil prior to, contemporaneously with, or after sowing seeds, after planting, or after plants have emerged from the ground. The inoculant can also be applied to seeds themselves prior to or at the time of planting (e.g., packaged seed may be sold with the inoculant already applied). The inoculant can also be applied to the plant after it has emerged from the ground, or to the leaves, stems, roots, or other parts of the plant.

The method for stimulating plant growth can include applying a substance such as glycerol, pyruvate, yeast extract, a polyol (e.g., mannitol, sorbitol, galactitol, fucitol, iditol, inositol, arabitol, xylitol, ribitol), polyethylene glycol or combination thereof to the plant growth medium. Any of the polyols can be used, with the preferred ones being mannitol and sorbitol. For the preparation of yeast extract, *Saccharomyces cerevisiae* is a preferred yeast starting material, although several other yeast strains may be useful to produce yeast ferment materials used in the compositions and methods described herein. Additional yeast strains that can be used instead of or in addition to *Saccharomyces cerevisiae* include *Kluyveromyces marxianus, Kluyveromyces lactis, Candida utilis* (Torula yeast), *Zygosaccharomyces, Pichia pastoris*, and *Hansanula polymorpha*, and others known to those skilled in the art.

In instances in which the substance is applied to a plant growth medium, at least one bacterial culture or at least one inoculum of the present invention can be applied to a plant or plant seed in the plant growth medium, or to the plant growth medium. Preferably, the inoculum is applied to the plant growth medium as a solid or liquid formulation. The bacterial culture or inoculum and the chemical can be applied contemporaneously or at separate times. The exact order is not of great relevance, and the optimal combination can be determined empirically by one of ordinary skill in the art without due experimentation. For example, a skilled artisan can set up experimental conditions wherein: (1) the inoculum or bacterial culture and the substance are administered concurrently, (2) the inoculum or bacterial culture is administered on a separate occasion after the substance is added to a plant growth medium, (3) the inoculum or bacterial culture is administered on a separate occasion prior to the substance being added to a plant growth medium, and the like. The results of such and similar experimental designs can easily demonstrate the most suitable methods for application of the bacterial strain or inoculum and the substance. Thus, the bacterial culture or inoculum of the present invention can be applied to a plant growth medium prior to, concurrently with, or after planting of seeds, seedlings, cuttings, bulbs, or plants in the plant growth medium.

The plant growth medium includes soil, water, an aqueous solution, sand, gravel, a polysaccharide, mulch, compost, peat moss, straw, logs, clay, or a combination thereof. Preferably, the plant growth medium is soil or compost. As is known in the art, the plant growth medium can be stored for future planting.

For purposes of the compositions and methods of the present invention, the plant can be a dicotyledon, a monocotyledon or a gymnosperm.

The dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, chrysanthemum, cinnamon, citron, clementine, clove, clover, coffee, cola nut, colza, corn, cotton, cottonseed, cowpea, crambe, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, lespedeza, lettuce, lime, liquorice, litchi, loquat, lupine, macadamia nut, mace, mandarin, mangel, mango, medlar, melon, mint, mulberry, mustard, nectarine, niger seed, nutmeg, okra, olive, opium, orange, papaya, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus *Cinchona*, quinoa, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, cassia, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, sassafras, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild betel, West African pepper, yerba santa, tarragon, parsley, chervil, land cress, burnet saxifrage, honeyherb, butterbur, shiso, water pepper, perilla, bitter bean, oca, kampong, Chinese celery, lemon basil, Thai basil, water mimosa, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

The dicotyledon can be from a family selected from the group consisting of Acanthaceae (acanthus), Aceraceae (maple), Achariaceae, Achatocarpaceae (achatocarpus), Actinidiaceae (Chinese gooseberry), Adoxaceae (moschatel), Aextoxicaceae, Aizoaceae (fig marigold), Akaniaceae, Alangiaceae, Alseuosmiaceae, Alzateaceae, Amaranthaceae (amaranth), Amborellaceae, Anacardiaceae (sumac), Ancistrocladaceae, Anisophylleaceae, Annonaceae (custard apple), Apiaceae (carrot), Apocynaceae (dogbane), Aquifoliaceae (holly), Araliaceae (ginseng), Aristolochiaceae (birthwort), Asclepiadaceae (milkweed), Asteraceae (aster), Austrobaileyaceae, Balanopaceae, Balanophoraceae (balanophora), Balsaminaceae (touch-me-not), Barbeyaceae, Barclayaceae, Basellaceae (basella), Bataceae (saltwort), Begoniaceae (begonia), Berberidaceae (barberry), Betulaceae (birch), Bignoniaceae (trumpet creeper), Bixaceae (lipstick tree), Bombacaceae (kapok tree), Boraginaceae (borage), Brassicaceae (mustard, also Cruciferae), Bretschneideraceae, Brunelliaceae (brunellia), Bruniaceae, Brunoniaceae, Buddlejaceae (butterfly bush), Burseraceae (frankincense), Buxaceae (boxwood), Byblidaceae, Cabombaceae (water shield), Cactaceae (cactus), Caesalpiniaceae, Callitrichaceae (water starwort), Calycanthaceae (strawberry shrub), Calyceraceae (calycera), Campanulaceae (bellflower), Canellaceae (canella), Cannabaceae (hemp), Capparaceae (caper), Caprifoliaceae (honeysuckle), Cardiopteridaceae, Caricaceae (papaya), Caryocaraceae (souari), Caryophyllaceae (pink), Casuarinaceae (she-oak), Cecropiaceae (cecropia), Celastraceae (bittersweet), Cephalotaceae, Ceratophyllaceae (hornwort), Cercidiphyllaceae (katsura tree), Chenopodiaceae (goosefoot), Chloranthaceae (chloranthus), Chrysobalanaceae (cocoa plum), Circaeasteraceae, Cistaceae (rockrose), Clethraceae (clethra), Clusiaceae (mangosteen, also Guttiferae), Cneoraceae, Columelliaceae, Combretaceae (Indian almond), Compositae (aster), Connaraceae (cannarus), Convolvulaceae (morning glory), Coriariaceae, Cornaceae (dogwood), Corynocarpaceae (karaka), Crassulaceae (stonecrop), Crossosomataceae (crossosoma), Crypteroniaceae, Cucurbitaceae (cucumber), Cunoniaceae (cunonia), Cuscutaceae (dodder), Cyrillaceae (cyrilla), Daphniphyllaceae, Datiscaceae (datisca), Davidsoniaceae, Degeneriaceae, Dialypetalanthaceae, Diapensiaceae (diapensia), Dichapetalaceae, Didiereaceae, Didymelaceae, Dilleniaceae (dillenia), Dioncophyllaceae, Dipentodontaceae, Dipsacaceae (teasel), Dipterocarpaceae (meranti), Donatiaceae, Droseraceae (sundew), Duckeodendraceae, Ebenaceae (ebony), Elaeagnaceae (oleaster), Elaeocarpaceae (elaeocarpus), Elatinaceae (waterwort), Empetraceae (crowberry), Epacridaceae (epacris), Eremolepidaceae (catkin-mistletoe), Ericaceae (heath), Erythroxylaceae (coca), Eucommiaceae, Eucryphiaceae, Euphorbiaceae (spurge), Eupomatiaceae, Eupteleaceae, Fabaceae (pea or legume), Fagaceae (beech), Flacourtiaceae (flacourtia), Fouquieriaceae (ocotillo), Frankeniaceae (frankenia), Fumariaceae (fumitory), Garryaceae (silk tassel), Geissolomataceae, Gentianaceae (gentian), Geraniaceae (geranium), Gesneriaceae (gesneriad), Globulariaceae, Gomortegaceae, Goodeniaceae (goodenia), Greyiaceae, Grossulariaceae (currant), Grubbiaceae, Gunneraceae (gunnera), Gyrostemonaceae, Haloragaceae (water milfoil), Hamamelidaceae (witch hazel), Hernandiaceae (hernandia), Himantandraceae, Hippocastanaceae (horse chestnut), Hippocrateaceae (hippocratea), Hippuridaceae (mare's tail), Hoplestigmataceae, Huaceae, Hugoniaceae, Humiriaceae, Hydnoraceae, Hydrangeaceae (hydrangea), Hydrophyllaceae (waterleaf), Hydrostachyaceae, Icacinaceae (icacina), Idiospermaceae, Illiciaceae (star anise), Ixonanthaceae, Juglandaceae (walnut), Julianiaceae, Krameriaceae (krameria), Lacistemataceae, Lamiaceae (mint, also Labiatae), Lardizabalaceae (lardizabala), Lauraceae (laurel), Lecythidaceae (brazil nut), Leeaceae, Leitneriaceae (corkwood), Lennoaceae (lennoa), Lentibulariaceae (bladderwort), Limnanthaceae (meadow foam), Linaceae (flax), Lissocarpaceae, Loasaceae (loasa), Loganiaceae (logania), Loranthaceae (showy mistletoe), Lythraceae (loosestrife), Magnoliaceae (magnolia), Malesherbiaceae, Malpighiaceae (barbados cherry), Malvaceae (mallow), Marcgraviaceae (shingle plant), Medusagynaceae, Medusandraceae, Melastomataceae (melastome), Meliaceae (mahogany), Melianthaceae, Mendonciaceae, Menispermaceae (moonseed), Menyanthaceae (buckbean), Mimosaceae, Misodendraceae, Mitrastemonaceae, Molluginaceae (carpetweed), Monimiaceae (monimia), Monotropaceae (Indian pipe), Moraceae (mulberry), Moringaceae (horseradish tree), Myoporaceae (myoporum), Myricaceae (bayberry), Myristicaceae (nutmeg), Myrothamnaceae, Myrsinaceae (myrsine), Myrtaceae (myrtle), Nelumbonaceae (lotus lily), Nepenthaceae (East Indian pitcherplant), Neuradaceae, Nolanaceae, Nothofagaceae, Nyctaginaceae (four-o'clock), Nymphaeaceae (water lily), Nyssaceae (sour gum), Ochnaceae (ochna), Olacaceae (olax), Oleaceae (olive), Oliniaceae, Onagraceae (evening primrose), Oncothecaceae, Opiliaceae, Orobanchaceae (broom rape), Oxalidaceae (wood sorrel), Paeoniaceae (peony), Pandaceae, Papaveraceae (poppy), Papilionaceae, Paracryphiaceae, Passifloraceae (passionflower), Pedaliaceae (sesame), Pellicieraceae, Penaeaceae, Pentaphragmataceae, Pentaphylacaceae, Peridiscaceae, Physenaceae, Phytolaccaceae (pokeweed), Piperaceae (pepper), Pittosporaceae (pittosporum), Plantaginaceae (plantain), Platanaceae (plane tree), Plumbaginaceae (leadwort), Podostemaceae (river weed), Polemoniaceae (phlox), Polygalaceae (milkwort), Polygonaceae (buckwheat), Portulacaceae (purslane), Primulaceae (primrose), Proteaceae (protea), Punicaceae (pomegranate), Pyrolaceae (shinleaf), Quiinaceae, Rafflesiaceae (rafflesia), Ranunculaceae (buttercup orranunculus), Resedaceae (mignonette), Retziaceae, Rhabdodendraceae, Rhamnaceae (buckthorn), Rhizophoraceae (red mangrove), Rhoipteleaceae, Rhynchocalycaceae, Rosaceae (rose), Rubiaceae (madder), Rutaceae (rue), Sabiaceae (sabia), Saccifoliaceae, Salicaceae (willow), Salvadoraceae, Santalaceae (sandalwood), Sapindaceae (soapberry), Sapotaceae (sapodilla), Sarcolaenaceae, Sargentodoxaceae, Sarraceniaceae (pitcher plant), Saururaceae (lizard's tail), Saxifragaceae (saxifrage), Schisandraceae (schisandra), Scrophulariaceae (figwort), Scyphostegiaceae, Scytopetalaceae, Simaroubaceae (quassia), Simmondsiaceae (jojoba), Solanaceae (potato), Sonneratiaceae (sonneratia), Sphaerosepalaceae, Sphenocleaceae (spenoclea), Stackhousiaceae (stackhousia), Stachyuraceae, Staphyleaceae (bladdernut), Sterculiaceae (cacao), Stylidiaceae, Styracaceae (storax), Surianaceae (suriana), Symplocaceae (sweetleaf), Tamaricaceae (tamarix), Tepuianthaceae, Tetracentraceae, Tetrameristaceae, Theaceae (tea), Theligonaceae, Theophrastaceae (theophrasta), Thymelaeaceae (mezereum), Ticodendraceae, Tiliaceae (linden), Tovariaceae, Trapaceae (water chestnut), Tremandraceae, Trigoniaceae, Trimeniaceae, Trochodendraceae, Tropaeolaceae (nasturtium), Turneraceae (turnera), Ulmaceae (elm), Urticaceae (nettle), Valerianaceae (valerian), Verbenaceae (verbena), Violaceae (violet), Viscaceae (Christmas mistletoe), Vitaceae (grape), Vochysiaceae, Winteraceae (wintera), Xanthophyllaceae, and Zygophyllaceae (creosote bush).

The monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, areca, bajra, betel nut, broom millet, broom sorghum, citronella, coconut, cocoyam, maize, dasheen, durra, durum wheat, edo, fique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Alternatively, the monocotyledon can be selected from a family selected from the group consisting of Acoraceae (calamus), Agavaceae (century plant), Alismataceae (water plantain), Aloeaceae (aloe), Aponogetonaceae (cape pondweed), Araceae (arum), Arecaceae (palm), Bromeliaceae (bromeliad), Burmanniaceae (burmannia), Butomaceae (flowering rush), Cannaceae (canna), Centrolepidaceae, Commelinaceae (spiderwort), Corsiaceae, Costaceae (costus), Cyanastraceae, Cyclanthaceae (Panama hat), Cymodoceaceae (manatee grass), Cyperaceae (sedge), Dioscoreaceae (yam), Eriocaulaceae (pipewort), Flagellariaceae, Geosiridaceae, Haemodoraceae (bloodwort), Hanguanaceae (hanguana), Heliconiaceae (heliconia), Hydatellaceae, Hydrocharitaceae (tape grass), Iridaceae (iris), Joinvilleaceae (joinvillea), Juncaceae (rush), Juncaginaceae (arrow grass), Lemnaceae (duckweed), Liliaceae (lily), Limnocharitaceae (water poppy), Lowiaceae, Marantaceae (prayer plant), Mayacaceae (mayaca), Musaceae (banana), Najadaceae (water nymph), Orchidaceae (orchid), Pandanaceae (screw pine), Petrosaviaceae, Philydraceae (philydraceae), Poaceae (grass), Pontederiaceae (water hyacinth), Posidoniaceae (posidonia), Potamogetonaceae (pondweed), Rapateaceae, Restionaceae, Ruppiaceae (ditch grass), Scheuchzeriaceae (scheuchzeria), Smilacaceae (catbrier), Sparganiaceae (bur reed), Stemonaceae (stemona), Strelitziaceae, Taccaceae (tacca), Thurniaceae, Triuridaceae, Typhaceae (cattail), Velloziaceae, Xanthorrhoeaceae, Xyridaceae (yellow-eyed grass), Zannichelliaceae (horned pondweed), Zingiberaceae (ginger), and Zosteraceae (eelgrass).

The gymnosperm can be selected from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

The stimulation of plant growth achieved by the present methods can be measured and demonstrated in a number of ways. Stimulation of plant growth can be shown in instances wherein the average height of the plant is increased by at least about 5%, by at least about 10%, by at least about 15% or by at least about 20% as compared to the average height of plants grown under the same conditions but that have not been treated with the bacterial culture or inoculant. Also, stimulation of plant growth can be shown in instances wherein the average leaf diameter of the leaves of plant is increased by at least about 5%, by at least about 10%, by at least about 15% or by at least about 20% as compared to the average leaf diameter of plants grown under the same conditions but that have not been treated with the bacterial culture or inoculant. Similarly, stimulation of plant growth can be shown in instances wherein the average root length of the plant is increased by at least about 5%, by at least about 10%, by at least about 15% or by at least about 20% as compared to the average root length of the plants grown under the same conditions but that have not been treated with the bacterial culture or inoculant.

The present invention is also directed to plant seeds, which are coated with any of the inoculums or bacteriologically pure bacterial cultures of the present invention. The seed can be from any of the plants discussed in the foregoing sections belonging to monocotyledons, dicotyledons or gymnosperms. The bacterial inoculant or culture can be applied to the seeds through the use of a suitable coating mechanism prior to the seeds being sold into commerce for planting. The process of coating seeds with such an inoculum is generally well known to those skilled in the art. For example, the bacteria can be mixed with a porous, chemically inert granular carrier as described by U.S. Pat. No. 4,875,921, which is incorporated herein by reference with respect to such carriers. Alternatively, the bacterial inoculant can be prepared with or without a carrier and sold as a separate inoculant to be inserted directly into the furrows into which the seed is planted. The process for inserting such inoculants directly into the furrows during seed planting is also generally well known in the art. The density of inoculation of these bacterial cultures onto seeds or into the furrows should be sufficient to populate the sub-soil region adjacent to the roots of the plant with viable bacterial growth.

The present invention also relates to kits for stimulating plant growth, which include an inoculum as described herein, and instructions for applying the inoculum to plants, plant seeds, or a plant growth medium. Kits containing inoculants of the invention will typically include one or more containers of the inoculant, and printed instructions for using the inoculant for promoting plant growth. The kit can also include tools or instruments for reconstituting, measuring, mixing, or applying the inoculant, and will vary in accordance with the particular formulation and intended use of the inoculant.

As shown in Example 10 and other tables, bacteria provide a good system in which to select mutations for desired characteristics. It is possible to force such mutations through proper selection of desirable traits, while retaining the desired plant growth-promoting capabilities in bacteria. Accordingly, traits that may be desirable to induce in bacterial strains disclosed herein by forcing mutations without affecting plant growth promotion include, but are not limited to, antibiotic resistance, heavy metal resistance, tolerance to heat and cold, high and low salt tolerance, metabolic deficiencies (such as requirements for certain amino acids), metabolic gain-of-function (such as the ability to metabolize polysaccharides or plastic compounds), ability to withstand desiccation, resistance to UV radiation, tolerance of manmade chemicals, ability to bind more tightly to plant roots, higher affinity for plants, increased ability to colonize plants, motility, ability to accept recombinant DNA, and ability to express exogenous proteins. These attributes can be garnered by use of selective pressure or through man-made manipulation of plant growth promoting bacteria's genetics.

Further details concerning the preparation of bacterial inoculants and methods for inoculating plants with bacterial inoculants are found in e.g. U.S. Pat. Nos. 5,586,411; 5,697,186; 5,484,464; 5,906,929; 5,288,296; 4,875,921; 4,828,600; 5,951,978; 5,183,759; 5,041,383; 6,077,505; 5,916,029; 5,360,606; 5,292,507; 5,229,114; 4,421,544; and 4,367,609, each of which is incorporated herein by reference with respect to such methods.

Having described the invention in detail, it will be apparent that modifications and variations are possible without departing from the scope of the invention defined in the appended claims.

EXAMPLES

The following non-limiting examples are provided to further illustrate the present invention.

Example 1: Isolation and Identification of Bacterial Strains

Soil samples from rhizospheres of the healthiest and most resistant potato (*Solanum tuberosum*), yellow summer squash (*Cucurbita pepo*), tomato (*Solanum lycopersicum*), and pole bean (*Phaseolus coccineus*) plants were collected, diluted in sterile water, and spread onto nutrient agar plates. Bacterial isolates that demonstrated high growth rates and were able to be passaged and propagated were selected for further study. The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten lettuce seeds per treatment were planted at a depth of 1 cm in loam top soil (Columbia, Mo.) that was sieved to remove large debris. Seeds were inoculated at planting in 4 cm pots with 0.5 µl of resuspended bacteria in water mixed into 10 ml of H$_2$O. Ten ml of H$_2$O was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. After one week, plant heights and leaf diameters, as well as overall health of the plants were collected. Initial screening of rhizosphere isolates resulted in obtaining greater than 200 distinct species of bacteria and fungi from the rhizosphere of the four plants. Some of the bacterial species are described in Table 2. Identified strains are indicated by their proper bacterial identifications. Other strains are indicated by their unknown identification number. Inoculants giving results near control (+/−2%) were left out of the table.

TABLE 2

Butterhead Lettuce

| Bacterial Inoculant | Avg. Height (cm) | Comparison | SEM |
|---|---|---|---|
| Uninoculated | 1.8 | Control | .07 |
| *Paracoccus kondratiavae* NC35 | 2 | 111.1% | .05 |
| *B. aryabhattai* CAP53 | 3.65 | 202.8% | .45 |
| *B. flexus* BT054 | 2.45 | 136.1% | .11 |
| *Bacillus mycoides* strain BT155 | 2.17 | 120.4% | .21 |
| *B. aryabhattai* CAP56 | 2.1 | 116.7% | .20 |
| *B. nealsonii* BOBA57 | 2.8 | 155.6% | .03 |
| *E. cloacae* CAP12 | 2.4 | 133.3% | .41 |
| Unknown 8 | 1.77 | 77.8% | .65 |
| Unknown 122 | 1.9 | 105.6% | .11 |

Bacterial strains that produced the greatest effect on the overall plant health and plant height in the initial lettuce trial were subjected to further identification. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3' (SEQ ID NO: 7), E1099R A 5'-GGG TTG CGC TCG TTG C-3' (SEQ ID NO: 8), and E1099R B 5'-GGG TTG CGC TCG TTA C-3' (SEQ ID NO: 9). PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 2. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and are listed in Table 3.

TABLE 3

| Test | *E. cloacae* CAP12 | *P. kondratiavae* NC35 | *B. aryabhattai* CAP53 | *B. flexus* BT054 | *B. mycoides* BT155 | *B. aryabhattai* CAP56 | *B. sp.* BOBA57 |
|---|---|---|---|---|---|---|---|
| Urease | − | − | − | − | − | − | + |
| Catalase | + | + | + | + | + | + | + |
| Oxidase | − | + | + | + | − | − | − |
| Nitrate | + | + | − | + | + | − | + |
| Growth, 5% NaCl | + | − | + | + | − | + | + |
| Growth, 7.5% NaCl | − | − | + | + | − | + | − |
| Growth, 42° C. | + | + | + | + | + | + | + |
| Growth, 50° C. | − | − | + | + | − | + | − |
| Growth, pH 5 | + | − | + | + | − | + | + |
| Growth, pH 9 | + | + | + | + | + | + | + |
| Acid, Cellobiose | + | − | + | + | + | + | − |
| Acid, Lactose | + | − | + | + | + | − | + |
| Acid, Starch | − | − | − | + | − | + | − |

TABLE 2-continued

Butterhead Lettuce

| Bacterial Inoculant | Avg. Height (cm) | Comparison | SEM |
|---|---|---|---|
| Unknown 15 | 1.4 | 77.8% | .41 |
| Unknown 39 | 1.8 | 100.0% | .20 |
| Unknown 401 | 2 | 111.1% | .21 |
| Unknown 402 | 1.53 | 85.2% | .27 |
| Unknown 41 | 1.45 | 80.6% | .31 |
| Unknown 42 | 1.4 | 77.8% | .15 |
| Unknown 44 | 2.2 | 133.3% | .08 |
| Unknown 51 | 1.83 | 102.9% | .21 |

Example 2: Isolation and Identification of Additional Bacterial Strains

Soil samples from agricultural fields near Gas, Kans. were collected, diluted in sterile water, and spread onto nutrient agar plates. Bacterial isolates that demonstrated high growth rates and were able to be passaged and propagated were selected for further study. The selected strains were grown in minimal media (KH$_2$PO$_4$ 3 g, Na$_2$HPO$_4$ 6 g, NH$_4$Cl 1 g, NaCl 0.50 g, MgSO$_4$ 7H$_2$O 0.15 g, CaCl$_2$ 2H$_2$O 0.013 g, and glucose 1 g, per L dry weight). Overnight cultures (30° C.) of selected strains were spun down, media decanted off, and resuspended in an equal amount of distilled water. Corn seeds were coated with commercial seed polymer mixed with water alone (1.6 µl per seed total) or commercial seed polymer containing selected bacterial strains (1.6 µl per seed total). Coated seeds were planted in (3 inch) 7.62 cm diameter pots at a depth of 1 inch (2.54 cm) in loam top soil (Columbia, Mo.) that was sieved to remove large debris. Plants were grown at temperatures between 18-24° C. (65-75° F.) with 11 hours of light/day, and 50 ml of watering at planting and every 3 days. After two weeks, plant heights and leaf diameters, as well as overall health of the plants were collected. For germination assays and determining 3 day root length, seeds were coated as indicated above and evenly dispersed at 10 seeds per paper towel. The paper towels were wetted with 10 mls of water, rolled up, placed in a small plastic bag and incubated at 30° C. or placed on a germination heat mat at 27-30° C. (80-85° F.). Root measurements were recorded after 3 days. Initial screening of rhizosphere isolates resulted in obtaining greater than 100 distinct species of bacteria and fungi from the rhizosphere. Some of the bacterial species are described in Table 4. Identified strains are indicated by their proper bacterial identifications.

TABLE 4

Corn Seed Treatments

| Bacterial Inoculant | Avg. Height (2 weeks) normalized to polymer control (%) | Avg. Root Length (3 days) normalized to polymer control (%) |
|---|---|---|
| Polymer control | 100 | 100 |
| B. mycoides EE118 | 111.1 | 189.1 |
| B. subtilis EE148 | 99.4 | 172.8 |
| Alcaligenes faecalis EE107 | 111.5 | 129.2 |
| B. mycoides EE141 | 109.2 | 143.5 |
| B. mycoides BT46-3 | 105.6 | 141.3 |
| B. cereus family member EE128 | 105.6 | — |
| B. thuringiensis BT013A | 101.8 | 103.8 |
| Paenibacillus massiliensis BT23 | 104.2 | 139.4 |
| B. cereus family member EE349 | 105.2 | — |
| B. subtilis EE218 | 106.6 | — |
| B. megaterium EE281 | 107.8 | — |

Bacterial strains that produced the greatest effect on plant health are described in Table 4. Bacterial strains were grown overnight in Luria Bertani broth at 37° C., and overnight cultures were spun down in a centrifuge. Media was decanted and the remaining bacterial pellet was subjected to chromosomal DNA isolation using the Qiagen Bacterial Chromosomal DNA Isolation kit. Chromosomal DNA was subjected to PCR amplification of the 16S rRNA coding regions using the primers E338F 5'-ACT CCT ACG GGA GGC AGC AGT-3', E1099R A 5'-GGG TTG CGC TCG TTG C-3' and E1099R B 5'-GGG TTG CGC TCG TTA C-3'. PCR amplicons were purified using a Promega PCR purification kit, and the resultant amplicons were diluted and sent to the University of Missouri DNA Core for DNA sequencing. DNA sequences were compared to the NCBI BLAST database of bacterial isolates, and genus and species were identified by direct comparison to known strains. Top identified species are indicated in Table 4. In many cases, 16S rRNA DNA sequences were only able to delineate the genus of the selected bacterial strain. In cases where a direct identification was not forthcoming, additional biochemistry analyses, using methods standard in the field, were performed to differentiate strains at the species and strain levels, and the differentiated strains are listed in Table 5.

TABLE 5

| Test | B. thuringiensis BT013A | B. cereus family member EE349 | B. subtilis EE148 | B. subtilis EE218 | B. megaterium EE281 | Paenibacillus massiliensis BT23 | B. mycoides BT46-3 | Alcaligenes faecalis EE107 | B. mycoides EE118 | B. cereus family member EE128 | B. mycoides EE141 |
|---|---|---|---|---|---|---|---|---|---|---|---|
| Motility | + | + | + | + | + | + | − | + | − | − | − |
| Rhizoid Colony | − | − | − | − | − | + | + | − | + | − | + |
| Catalase | + | + | + | + | + | + | + | + | + | + | + |
| Oxidase | + | − | − | − | − | − | − | + | − | − | − |
| Nitrate | + | + | wk | − | − | + | + | + | + | + | + |
| Growth, 5% NaCl | + | wk | − | + | + | − | + | + | − | + | − |
| Growth, 7.5% NaCl | wk | − | − | + | + | − | − | − | − | − | − |
| Growth, 42° C. | − | + | + | + | + | + | + | + | − | + | − |
| Growth, 50° C. | − | − | − | − | − | − | − | − | − | − | − |
| Growth, pH 5 | wk | + | + | + | + | − | wk | + | − | + | − |
| Growth, pH 9 | + | + | − | + | + | − | wk | + | + | + | − |
| Acid, Cellobiose | − | − | wk | + | − | + | + | wk | + | − | wk |
| Acid, Lactose | − | + | + | + | + | − | + | + | − | + | wk |
| Acid, Starch | − | + | − | + | + | − | + | wk | + | + | − | wk = weak growth or low growth

Example 3: Testing of Bacteria of the Present Invention on Alfalfa

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and bacteria resuspended in an equal amount of distilled water. Ten Zeba-coated alfalfa seeds were planted for each treatment at a depth of 0.6 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Alfalfa was allowed to grow for 1 week to analyze emergence and initial outgrowth of plants under described conditions. Identified strains indicated by their proper bacterial identifications and final height data are listed in Table 6.

TABLE 6

| | Alfalfa | | |
|---|---|---|---|
| Bacterial Inoculant | Avg. Height (cm) | Comparison | SEM |
| Uninoculated | 4.82 | — | .008 |
| B. aryabhattai CAP56 | 4.85 | 101.20% | .016 |
| B. nealsonii BOBA57 | 4.86 | 101.70% | .021 |
| E. cloacae CAP12 | 5.6 | 116.23% | .020 |

Example 4: Testing of Bacteria of the Present Invention on Cucumbers

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in equal amount of distilled water. Ten cucumber seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Cucumbers were allowed to grow for 2 weeks to analyze emergence and initial outgrowth of plants under described conditions. Identified strains indicated by their proper bacterial identifications and final height data are listed in Table 7.

TABLE 7

| | Cucumbers | | |
|---|---|---|---|
| Bacterial Inoculant | Avg. Height (cm) | Comparison | SEM |
| Uninoculated | 11.23 | — | .067 |
| B. aryabhattai CAP53 | 11.5 | 102.00% | .023 |
| B. aryabhattai CAP56 | 11.35 | 101.20% | .035 |
| B. nealsonii BOBA57 | 11.33 | 101.10% | .014 |

Example 5: Testing of Bacteria of the Present Invention on Yellow Squash

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten yellow squash seeds were planted for each treatment at a depth of 1 cm in loam top soil (Columbia, Mo.) that was sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 in$^3$ (7.62 cm$^3$) of soil as well as saturate the soil for proper germination of seeds. Plants were grown at temperatures between 65-75° F. (18-24° C.) with 11 hours of light/day, and 5 ml of watering every 3 days. Squash was allowed to grow for 2 weeks to analyze emergence and initial outgrowth of plants under described conditions. Identified strains indicated by their proper bacterial identifications, final height data, and final leaf diameter (by span of the two leaves) data are listed in Table 8.

TABLE 8

| | Yellow Squash | | | | |
|---|---|---|---|---|---|
| Bacterial Inoculant | Avg. Height (cm) | Comparison | SEM | Leaf Diameter (cm) | Comparison |
| Uninoculated | 10.16 | — | .028 | 5.08 | — |
| B. aryabhattai CAP53 | 11.75 | 115.60% | .055 | 7.25 | 142.60% |
| B. flexus BT054 | 11.88 | 116.90% | .017 | 6.36 | 125.20% |
| Bacillus mycoides BT155 | 11.92 | 117.20% | .051 | 6.33 | 124.60% |
| B. aryabhattai CAP56 | 11.95 | 117.60% | .027 | 6.33 | 124.60% |
| B. nealsonii BOBA57 | 11.89 | 117.00% | .118 | 6.42 | 126.40% |
| E. cloacae CAP12 | 11.42 | 112.30% | .039 | 6.83 | 134.40% |

Example 6: Testing of Bacteria of the Present Invention on Ryegrass

The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Thirty ryegrass seeds were planted for each treatment at a depth of 0.3 cm in loam top soil (Columbia, Mo.) that was sieved to remove large debris. Seeds were inoculated at planting with 0.5 µl of resuspended bacteria in water mixed into 10 ml of $H_2O$. Ten ml of H₂O was sufficient to deliver the bacteria into the 3 in³ (7.62 cm³) of soil as well as saturate the soil for proper germination of seeds. Plants were grown at temperatures between 65-75° F. (18-24° C.) with 11 hours of light/day, and 5 ml of watering every 3 days. Ryegrass was allowed to grow for 1.5 weeks to analyze emergence and initial outgrowth of plants under described conditions. Identified strains indicated by their proper bacterial identifications and height data are listed in Table 9.

TABLE 9

| | Ryegrass | | |
|---|---|---|---|
| Bacterial Inoculant | Avg. Height (cm) | Comparison | SEM |
| Uninoculated | 1.61 | — | .023 |
| B. aryabhattai CAP53 | 2.01 | 124.70% | .012 |
| B. flexus BT054 | 2.21 | 137.30% | .034 |
| Bacillus mycoides BT155 | 2.29 | 142.20% | |
| B. aryabhattai CAP56 | 2.19 | 136.00% | .009 |
| B. nealsonii BOBA57 | 2.29 | 142.40% | .045 |
| E. cloacae CAP12 | 1.98 | 122.50% | .015 |

Example 7: Testing of Bacteria of the Present Invention on Corn

The selected strains were grown in minimal media (KH₂PO₄ 3 g, Na₂HPO₄ 6 g, NH₄Cl 1 g, NaCl 0.50 g, MgSO₄ 7H₂O 0.15 g, CaCl₂ 2H₂O 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of H₂O. Ten ml of H₂O was sufficient to deliver the bacteria into the 3 in³ (7.62 cm³) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 10.

TABLE 10

| | Corn | | |
|---|---|---|---|
| Bacterial Inoculant | Avg. Height (cm) | Comparison | SEM |
| Uninoculated | 8.9 | — | .039 |
| B. aryabhattai CAP53 | 11.01 | 123.60% | .081 |
| B. flexus BT054 | 9.96 | 112.00% | .095 |
| Bacillus mycoides strain BT155 | 9.6 | 107.90% | .041 |
| B. aryabhattai CAP56 | 9.54 | 107.10% | .088 |
| B. nealsonii BOBA57 | 9.23 | 103.70% | .077 |

Example 8: Testing of Bacteria on Soybeans

The selected strains were grown in minimal media (KH₂PO₄ 3 g, Na₂HPO₄ 6 g, NH₄Cl 1 g, NaCl 0.50 g, MgSO₄ 7H₂O 0.15 g, CaCl₂ 2H₂O 0.013 g, and glucose 1 g, per L dry weight, or for Bradyrhizobium or Rhizobium on yeast mannitol media). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of H₂O. When testing two bacterial strains, 0.5 µl of each resuspended bacteria was mixed into 10 ml of H₂O. Ten ml of H₂O was sufficient to deliver the bacteria into the 3 in³ (7.62 cm³) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 11. Co-inoculation of bacteria strains in the present invention with members of the Bradyrhizobium sp. or Rhizobium sp. lead to an increase in plant growth compared to either inoculant alone.

TABLE 11

| | Soybeans | | |
|---|---|---|---|
| Bacterial Inoculant | Avg. Height (cm) | Comparison | SEM |
| Uninoculated | 13.94 | — | .089 |
| B. aryabhattai CAP53 | 16.32 | 117.1% | .146 |
| B. flexus BT054 | 17.85 | 128.0% | .177 |
| Bacillus mycoides strain BT155 | 18.93 | 135.8% | .117 |
| B. aryabhattai CAP56 | 17.23 | 123.6% | .133 |
| B. aryabhattai CAP53 | 16.32 | 117.1% | .077 |
| B. aryabhattai CAP53 and Bradyrhizobium sp. | 16.72 | 119.9% | .182 |
| B. aryabhattai CAP53 and Rhizobium sp. | 17.32 | 124.2% | .086 |
| Bradyrhizobium sp. | 14.25 | 102.2% | |
| Rhizobium sp. | 14.75 | 105.8% | |

Example 9: Testing of Bacteria of the Present Invention on Soybeans with the Additive Effect of Plant-Growth-Promoting Chemicals The selected strains were grown in minimal media (KH₂PO₄ 3 g, Na₂HPO₄ 6 g, NH₄Cl 1 g, NaCl 0.50 g, MgSO₄ 7H₂O 0.15 g, CaCl₂ 2H₂O 0.013 g, and glucose 1 g, per L dry weight). Overnight cultures (30° C.) of selected strains were spun down, media decanted off, and resuspended in equal amount of distilled water. Ten soybean seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of H₂O alone, into 10 ml of H₂O with 0.5 µl glycerol, into 10 ml of H₂O with 0.5 µl 2,3-butanediol, or into 10 ml of H₂O with 0.5 mg yeast extract. Ten ml of H₂O was sufficient to deliver the bacteria into the 3 in³ (7.62 cm³) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 12.

TABLE 12

Soybeans

| Bacterial Inoculant | Avg. Height (cm) | Comparison to Uninoculated | Comparison to Inoculant | SEM |
|---|---|---|---|---|
| Uninoculated | 11.24 | — | | .153 |
| Uninoculated and Glycerol | 12.34 | 109.8% | | .107 |
| Uninoculated and Yeast Extract | 14.03 | 124.8% | | .212 |
| B. aryabhattai CAP53 | 12.56 | 111.7% | — | .146 |
| B. aryabhattai CAP53 and Glycerol | 13.22 | 117.6% | 105.3% | .118 |
| B. aryabhattai CAP53 and Yeast Extract | 14.73 | 131.0% | 117.3% | .119 |
| Paracoccus sp. NC35 | 13.32 | 118.5% | — | .027 |
| Paracoccus sp. NC35 and 2,3-butanediol | 15.09 | 134.3% | 113.3% | .210 |
| Paracoccus sp. NC35 and Yeast Extract | 15.83 | 140.8% | 118.8% | .145 |

Example 10: Testing of Bacteria of the Present Invention on Corn with the Additive Effect of Plant-Growth-Promoting Chemicals The selected strains were grown in minimal media ($KH_2PO_4$ 3 g, $Na_2HPO_4$ 6 g, $NH_4Cl$ 1 g, NaCl 0.50 g, $MgSO_4$ $7H_2O$ 0.15 g, $CaCl_2$ $2H_2O$ 0.013 g, and glucose 1 g, per L dry weight). Overnight cultures (30° C.) of selected strains were spun down, media decanted off, and resuspended in an equal amount of distilled water. Ten corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of $H_2O$ alone, into 10 ml of $H_2O$ with 0.5 µl 2,3-butanediol, or into 10 ml of $H_2O$ with 0.5 mg yeast extract. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Corn was allowed to grow for 2 weeks to analyze emergence and initial outgrowth of plants under described conditions. Identified strains indicated by their proper bacterial identifications and final height data are listed in Table 13.

TABLE 13

Corn

| Bacterial Inoculant | Avg. Height (cm) | Comparison to Uninoculated | Comparison to Inoculant | SEM |
|---|---|---|---|---|
| Uninoculated | 15.15 | — | | .156 |
| Uninoculated and 2,3-butanediol | 16.03 | 105.8% | | .078 |
| Uninoculated and Yeast Extract | 17.04 | 112.5% | | .101 |
| Paracoccus sp. NC35 | 16.04 | 105.9% | — | .023 |
| Paracoccus sp. NC35 and 2,3-butanediol | 16.24 | 107.2% | 101.2% | .111 |
| Paracoccus sp. NC35 and Yeast Extract | 17.96 | 118.5% | 112.0% | .127 |

Example 11: Generation of Mutants Able to Grow in High Salt Conditions that Retain Plant Growth-Promoting Ability Using Selective Pressure Paracoccus kondratiavae NC35 and Bacillus mycoides BT155 were found to be salt sensitive and not very active in high salt soil types (Table 3). To induce salt tolerance in these plant growth promoting bacteria, a selective pressure using successively higher concentrations of NaCl was used to find mutants that could tolerate these high salt soil types. The selected strains were grown in Luria Bertani liquid media at 37° C. overnight and plated on 1% NaCl salt agar media and allowed to grow for 48 hours at 30° C. Individual colonies of strains that survived on the 1% salt LB agar plates were grown in Luria Bertani with 1% NaCl liquid media at 37° C. overnight and plated on 3% NaCl salt LB agar media for 48 hours at 30° C. Colonies of strains that survived on the 3% NaCl salt LB agar were grown in Luria Bertani with 3% NaCl liquid media at 37° C. overnight and plated on 5% NaCl salt LB agar media and allowed to grow for 48 hours at 30° C. Bacterial colonies selected from the 5% salt LB agar plates were grown in Luria Bertani overnight plus 5% NaCl media at 37° C. Overnight cultures of original strains in minimal media and salt-tolerant mutants were grown overnight and were spun down, media decanted off, and resuspended in equal amount of distilled water. Nine soybean seeds were planted for each treatment at a depth of 2.5 cm in loam top soil (Columbia, Mo.) or loam supplemented with 5% salt solution (w/w), wherein both of the soils were sieved to remove large debris. Seeds were inoculated at planting with 0.5 µl of resuspended bacteria in water mixed into 10 ml of $H_2O$. Ten ml of $H_2O$ was sufficient to deliver the bacteria into the 3 $in^3$ (7.62 $cm^3$) of soil as well as saturate the soil for proper germination of seeds. Plants were grown at temperatures between 65-75° F. (18-24° C.) with 11 hours of light/day, and 5 ml of watering every 3 days. Soybeans were allowed to grow for 2 weeks to analyze emergence and initial outgrowth of plants under described conditions. Identified strains indicated by their proper bacterial identifications and final height data are listed in Table 14. Mutations were forced in a salt-sensitive strain that retained plant growth-promoting ability.

TABLE 14

| Bacterial Inoculant | Avg. Height, Loam Soil (cm) | Percentage | Avg. height, 5% Salt Soil (cm) | Percentage | SEM, Loam Soil | SEM, 5% Salt Soil |
|---|---|---|---|---|---|---|
| H$_2$O Control | 10.54 | 100% | 7.34 | 100% | .322 | .117 |
| Paracoccus sp NC35, salt sensitive | 11.91 | 113% | 7.15 | 97.4% | .115 | .215 |
| Paracoccus sp. NC35 salt-tolerant | 12.02 | 114% | 9.23 | 125.7% | .451 | .105 |
| Bacillus mycoides strain BT155, salt sensitive | 12.75 | 120.9% | 7.45 | 101.5% | .212 | .279 |
| Bacillus mycoides strain BT155, salt-tolerant | 12.92 | 122.6% | 8.93 | 121.7% | .185 | .056 |

Example 12: Generation of Mutants Able to Grow in the Presence of Thiram that Retained Plant Growth-Promoting Ability Using Selective Pressure Thiram is a common well-established insecticide and fungicide used on a wide range of agriculture crops. Thiram is also quite antibacterial, and can have deleterious effects on most plant growth promoting bacteria, including those described herein. All strains tested were found to have a high degree of thiram sensitivity. Several of the strains, including the salt resistant Paracoccus kondratiavae NC35 from Example 11, Bacillus arybhattai CAP53, the salt resistant Bacillus mycoides BT155 from Example 11, and Bacillus thuringiensis BT0013A were grown in LB media with minute quantities of thiram (0.05 mg/L). Growth under these condition took four days, rather than the typical 12 hours in the absence of thiram. The mutated bacteria that began to grow in the presence of thiram were sequentially subjected to higher and higher concentrations of thiram (0.25 mg/L, 0.50 mg/L, 1 mg/L, 5 mg/L). Upon achieving a mutated culture that could withstand the highest amount of thiram on the seed (0.05 mg/seed), Paracoccus kondratiave NC35, the NC35 thiram (ThR)/salt resistant mutant, Bacillus arybhattai CAP53, the CAP53 ThR mutant, Bacillus mycoides BT155, the BT155 salt/ThR mutant, Bacillus thuringiensis BT013A and BT013A ThR mutant were applied on seeds in the presence of thiram at 0.05 mg/seed. Overnight cultures of original strains in minimal media and thiram-resistant mutants were grown overnight and were spun down, media decanted off, and resuspended in equal amount of distilled water. Ten soybean seeds were planted for each treatment at a depth of 2.5 cm in loam top soil (Columbia, Mo.) in standard seed treatment with 0.5 mg/seed thiram. Plants were grown at temperatures between 18-24° C. (65-75° F.) with 11 hours of light/day, and 5 ml of watering every 3 days. Soybeans were allowed to grow for 2 weeks to analyze emergence and initial outgrowth of plants under described conditions. Mutations were forced in all strains that retained plant growth-promoting ability. Results are shown in Table 15 below.

TABLE 15

| Bacterial Inoculant | Percentage | SEM, |
|---|---|---|
| H$_2$O Control | 100% | 3.4% |
| Paracoccus sp NC35, thiram sensitive | 114.3% | 7.1% |
| Paracoccus sp. NC35 ThR, thiram-resistant | 135.3% | 9.2% |
| Bacillus aryabhattai CAP53, thiram sensitive | 107.6% | 10.1% |
| Bacillus aryabhattai CAP53 ThR thiram-resistant | 111.9% | 7.2% |
| Bacillus mycoides BT155, thiram sensitive | 103.9% | 6.9% |
| Bacillus mycoides BT155, ThR thiram-resistant | 124.1% | 12.3% |
| Bacillus thuringiensis BT013A, thiram sensitive | 100.1% | 5.7% |
| Bacillus thuringiensis BT013A, ThR, thiram-resistant | 104.9% | 8.3% |

Example 13: Generation of Mutants Able to Grow in the Presence of Glyphosate that Retained Plant Growth-Promoting Ability Using Selective Pressure Glyphosate is a common well-established herbicide used on a wide range of agriculture crops. Glyphosate is also quite inhibitory to various bacteria, and can have deleterious effects on some plant growth promoting bacteria, including those described herein. Two of the strains described herein had a degree of inhibition in the presence of glyphosate. Bacillus arybhattai CAP53 were grown in LB media with minute quantities of glyphosate (0.05 mg/L). Growth under these conditions took two days, rather than the typical 12 hours in the absence of glyphosate. The mutated bacteria that began to grow in the presence of glyphosate were sequentially subjected to higher and higher concentrations of glyphosate (0.25 mg/L, 0.50 mg/L, 1 mg/L, 5 mg/L). Upon achieving a mutated culture that could withstand a higher amount of glyphosate in the soil (100 ppm), Bacillus aryhbhattai CAP53 glyphosate-tolerant and wild type strains were applied to seeds at a rate of 1×10$^5$ CFU/seed with a standard seed treatment. Ten soybean seeds were planted for each treatment at a depth of 2.5 cm in loam top soil (Columbia, Mo.) in standard seed treatment with 100 ppm glyphosate. Plants were grown at temperatures between 18-24° C. (65-75° F.) with 11 hours of light/day, and 5 ml of watering every 3 days. Soybeans were allowed to grow for 2 weeks to analyze emergence and initial outgrowth of plants under described conditions. Mutations were forced in all strains that retained plant growth-promoting ability.

TABLE 16

| Bacterial Inoculant | Percentage | SEM, |
|---|---|---|
| H$_2$O Control | 100% | 7.4% |
| Bacillus aryabhattai CAP53, glyphosate sensitive | 107.4% | 5.8% |
| Bacillus aryabhattai CAP53, glyphosate-tolerant, GlyR | 110.5% | 4.6% |

Example 14: Bacillus cereus Family Members with Plant Growth Promoting Attributes

*Bacillus mycoides* strain BT155, *Bacillus mycoides* strain EE118, *Bacillus mycoides* strain EE141, *Bacillus mycoides* strain BT46-3, *Bacillus cereus* family member strain EE349, *Bacillus thuringiensis* strain BT013A, and *Bacillus megaterium* strain EE281 were grown in Luria Bertani broth at 37° C. and overnight cultures were spun down, media decanted off, and resuspended in equal amount of distilled water. 20 corn seeds were planted for each treatment at a depth of 2.5 cm in loam top soil (Columbia, Mo.) that was sieved to remove large debris. Seeds were inoculated at planting with 0.5 µl of resuspended bacteria in water mixed into 10 ml of H$_2$O. Fifty ml of H$_2$O was sufficient to deliver the bacteria into the 29 in$^3$ (442.5 cm$^3$) of soil as well as saturate the soil for proper germination of seeds. Plants were grown at temperatures between 65-72° F. with 13 hours of light/day, and 5 ml of watering every 3 days. Seedlings were allowed to grow for 2 weeks to analyze emergence and initial outgrowth of plants under described conditions. Identified strains indicated by their proper bacterial identifications and final height data are listed in Table 17.

TABLE 17

| Bacterial Inoculant | Avg. Height, cm, Corn | Percentage | SEM, |
|---|---|---|---|
| H2O Control | 11.41 | 100% | .123 |
| B. mycoides EE118 | 12.43 | 108.9% | .207 |
| B. mycoides EE141 | 12.84 | 112.5% | .231 |
| B. mycoides BT46-3 | 11.81 | 103.5% | .089 |
| Bacillus thuringiensis BT013A | 12.05 | 105.6% | .148 |
| Bacillus cereus family member EE128 | 13.12 | 114.9% | .159 |
| Bacillus mycoides BT155 | 12.85 | 112.6% | .163 |
| Bacillus megaterium EE281 | 11.99 | 105.1% | .098 |

All plant growth promoting bacteria tested had a beneficial effect on corn height at two weeks under the described conditions. The *Bacillus cereus* family member EE128 strain had the greatest effect in this trial, giving a greater than at 14% boost in corn height. When introducing elements of the present invention, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method for stimulating plant growth comprising applying a bacterial culture to a plant, plant seed, or plant growth medium, wherein the bacteria in the bacterial culture comprise:
   (a) *Bacillus mycoides* strain BT155 (NRRL No. B-50291);
   (b) *Bacillus mycoides* strain EE118 (NRRL No. B-50918);
   (c) *Bacillus subtilis* strain EE148 (NRRL No. B-50927);
   (d) *Alcaligenes faecalis* strain EE107 (NRRL No. B-50920);
   (e) *Bacillus mycoides* strain EE141 (NRRL No. B-50916);
   (f) *Bacillus mycoides* strain BT46-3 (NRRL No. B-50922);
   (g) *Bacillus cereus* family member strain EE128 (NRRL No. B-50917);
   (h) *Bacillus thuringiensis* strain BT013A (NRRL No. B-50924);
   (i) *Paenibacillus massiliensis* strain BT23 (NRRL No. B-50923);
   (j) *Bacillus cereus* family member strain EE349 (NRRL No. B-50928);
   (k) *Bacillus subtilis* strain EE218 (NRRL No. B-50926);
   (l) *Bacillus megaterium* strain EE281 (NRRL No. B-50925);

(m) salt-tolerant and thiram-resistant *Paracoccus* sp. strain NC35 (NRRL No. B-50948);

(n) salt-tolerant and thiram resistant *Bacillus mycoides* strain BT155 (NRRL No. B-50949);

(o) thiram-resistant *Bacillus aryabhattai* strain CAP53 (NRRL No. B-50946);

(p) thiram-resistant *Bacillus thuringiensis* strain BT013A (NRRL No. B-50947); or (q) glyphosate-tolerant *Bacillus aryabhattai* strain CAP53 (NRRL No. B-50945).

2. A method of claim 1, wherein the bacteria in the bacterial culture are mutants having all of the identifying characteristics of any of strains (a) through (l), wherein the mutants comprise one or more mutations and retain the ability to promote plant growth.

3. A method of claim 2, wherein the mutant comprises a salt-tolerant mutant, a thiram-resistant mutant, a glyphosate-tolerant mutant, or a mutant with a combination of mutations to impart salt tolerance, thiram resistance and/or glyphosate tolerance.

4. A method of claim 1, comprising applying the bacterial culture to plant seeds.

5. A method of claim 1, wherein the bacterial culture is applied in an inoculum comprising an effective amount of the bacterial culture and an agriculturally acceptable carrier.

6. A method of claim 1, wherein the bacterial culture is a biologically pure bacterial culture.

7. A method of claim 1, wherein the bacteria in the bacterial culture comprise *Bacillus thuringiensis* strain BT013A and the bacteria have a 16S ribosomal RNA sequence having at least about 99% sequence identity with the sequence of SEQ ID NO: 16.

8. A method of claim 1, wherein the bacteria in the bacterial culture comprise *Bacillus thuringiensis* strain BT013A.

9. A method of claim 1, wherein the bacteria in the bacterial culture comprise *Bacillus cereus* family member strain EE349.

10. A method of claim 1, wherein the bacterial in the bacterial culture comprise *Bacillus cereus* family member strain EE349 and the bacteria have a 16S ribosomal RNA sequence having at least about 99% sequence identity with the sequence of SEQ ID NO: 18.

11. A method of claim 5, wherein the inoculum comprises an effective amount of a mixture comprising at least two of the bacterial cultures.

12. A method of claim 5, wherein the inoculum further comprises an effective amount of a rhizobacteria.

13. A method of claim 12, wherein the rhizobacteria comprises *Bradyrhizobium* genus bacteria, *Rhizobium* genus bacteria, or a combination thereof.

14. A method of claim 13, wherein the *Bradyrhizobium* genus bacteria comprises *Bradyrhizobium japonicum.*

15. A method of claim 13, wherein the *Rhizobium* genus bacteria comprises *Rhizobium phaseoli, Rhizobium leguminosarum*, or a combination thereof.

16. A method of claim 5, wherein the agriculturally acceptable carrier comprises a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof.

17. A method of claim 5, wherein the agriculturally acceptable carrier comprises vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

18. A method of claim 5, wherein the inoculum is formulated as a seed coating formulation, a liquid formulation for application to plants or to a plant growth medium, or a solid formulation for application to plants or to a plant growth medium.

19. A method of claim 18, wherein the seed coating formulation is an aqueous or oil-based solution for application to seeds.

20. A method of claim 18, wherein the seed coating formulation is a powder or granular formulation for application to seeds.

21. A method of claim 18, wherein the liquid formulation for application to plants or to a plant growth medium is in a concentrated formulation or a ready-to-use formulation.

22. A method of claim 18, wherein the solid formulation for application to plants or to a plant growth medium is a granular formulation or a powder agent.

23. A method of claim 5, wherein the inoculum further comprises a fertilizer, a micronutrient fertilizer material, an insecticide, a herbicide, a plant growth amendment, a fungicide, a molluscicide, an algicide, an additional bacterial inoculant, a fungal inoculant, or a combination thereof.

24. A method of claim 23, wherein the insecticide comprises an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

25. A method of claim 23, wherein the fungicide comprises a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

26. A method of claim 23, wherein the additional bacterial inoculant comprises a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

27. An inoculum for application to plants, plant seeds, or a plant growth medium, wherein the inoculum comprises an effective amount of a bacterial culture, an agriculturally acceptable carrier, and a fungicide, wherein the bacteria in the bacterial culture comprise:

(a) *Bacillus mycoides* strain BT155 (NRRL No. B-50291);

(b) *Bacillus mycoides* strain EE118 (NRRL No. B-50918);

(c) *Bacillus subtilis* strain EE148 (NRRL No. B-50927);

(d) *Alcaligenes faecalis* strain EE107 (NRRL No. B-50920);
(e) *Bacillus mycoides* strain EE141 (NRRL No. B-50916);
(f) *Bacillus mycoides* strain BT46-3 (NRRL No. B-50922);
(g) *Bacillus cereus* family member strain EE128 (NRRL No. B-50917);
(h) *Bacillus thuringiensis* strain BT013A (NRRL No. B-50924);
(i) *Paenibacillus massiliensis* strain BT23 (NRRL No. B-50923);
(j) *Bacillus cereus* family member strain EE349 (NRRL No. B-50928);
(k) *Bacillus subtilis* strain EE218 (NRRL No. B-50926);
(l) *Bacillus megaterium* strain EE281 (NRRL No. B-50925);
(m) salt-tolerant and thiram-resistant *Paracoccus* sp. strain NC35 (NRRL No. B-50948);
(n) salt-tolerant and thiram resistant *Bacillus mycoides* strain BT155 (NRRL No. B-50949);
(o) thiram-resistant *Bacillus aryabhattai* strain CAP53 (NRRL No. B-50946);
(p) thiram-resistant *Bacillus thuringiensis* strain BT013A (NRRL No. B-50947); or
(q) glyphosate-tolerant *Bacillus aryabhattai* strain CAP53 (NRRL No. B-50945);
and wherein the fungicide comprises a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

28. A plant seed coated with the inoculum of claim 27.

29. An inoculum of claim 27, wherein the bacteria in the bacterial culture comprise *Bacillus thuringiensis* strain BT013A and the bacteria have a 16S ribosomal RNA sequence having at least about 99% sequence identity with the sequence of SEQ ID NO: 16.

30. An inoculum of claim 27, wherein the bacterial culture is a biologically pure bacterial culture.

31. A plant seed of claim 28, wherein the bacteria in the bacterial culture comprise *Bacillus thuringiensis* strain BT013A and the bacteria have a 16S ribosomal RNA sequence having at least about 99% sequence identity with the sequence of SEQ ID NO: 16.

32. A plant seed of claim 28, wherein the bacterial culture is a biologically pure bacterial culture.

33. A plant seed of claim 28, wherein the bacteria in the bacterial culture are mutants having all of the identifying characteristics of any of strains (a) through (l), wherein the mutants comprise one or more mutations and retain the ability to promote plant growth.

34. A plant seed of claim 33, wherein the mutant comprises a salt-tolerant mutant, a thiram-resistant mutant, a glyphosate-tolerant mutant, or a mutant with a combination of mutations to impart salt tolerance, thiram resistance and/or glyphosate tolerance.

35. A plant seed of claim 28, wherein the inoculum comprises an effective amount of a mixture comprising at least two of the bacterial cultures.

36. A plant seed of claim 28, wherein the inoculum further comprises an effective amount of a rhizobacteria.

37. A plant seed of claim 36, wherein the rhizobacteria comprises *Bradyrhizobium* genus bacteria, *Rhizobium* genus bacteria, or a combination thereof.

38. A plant seed of claim 37, wherein the *Bradyrhizobium* genus bacteria comprises *Bradyrhizobium japonicum*.

39. A plant seed of claim 37, wherein the *Rhizobium* genus bacteria comprises *Rhizobium phaseoli, Rhizobium leguminosarum*, or a combination thereof.

40. A plant seed of claim 28, wherein the agriculturally acceptable carrier comprises a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof.

41. A plant seed of claim 28, wherein the seed is coated with an aqueous solution, an oil-based solution, a powder formulation, or a granular formulation.

42. A plant seed of claim 28, wherein the inoculum further comprises a fertilizer, a micronutrient fertilizer material, an insecticide, a herbicide, a plant growth amendment, a molluscicide, an algicide, an additional bacterial inoculant, a fungal inoculant, or a combination thereof.

43. A plant seed of claim 42, wherein the insecticide comprises an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

44. A plant seed of claim 42, wherein the additional bacterial inoculant comprises a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

45. An inoculum of claim 27, wherein the bacteria in the bacterial culture comprises:
(a) *Bacillus mycoides* strain BT155 (NRRL No. B-50291);
(b) *Bacillus mycoides* strain EE118 (NRRL No. B-50918);
(c) *Bacillus subtilis* strain EE148 (NRRL No. B-50927);
(d) *Alcaligenes faecalis* strain EE107 (NRRL No. B-50920);
(e) *Bacillus mycoides* strain EE141 (NRRL No. B-50916);
(f) *Bacillus mycoides* strain BT46-3 (NRRL No. B-50922);
(g) *Bacillus cereus* family member strain EE128 (NRRL No. B-50917);
(h) *Paenibacillus massiliensis* strain BT23 (NRRL No. B-50923);
(i) *Bacillus cereus* family member strain EE349 (NRRL No. B-50928);
(j) *Bacillus subtilis* strain EE218 (NRRL No. B-50926);
(k) *Bacillus megaterium* strain EE281 (NRRL No. B-50925);

(l) salt-tolerant and thiram-resistant *Paracoccus* sp. strain NC35 (NRRL No. B-50948);
(m) salt-tolerant and thiram resistant *Bacillus mycoides* strain BT155 (NRRL No. B-50949);
(n) thiram-resistant *Bacillus aryabhattai* strain CAP53 (NRRL No. B-50946);
(o) thiram-resistant *Bacillus thuringiensis* strain BT013A (NRRL No. B-50947); or
(p) glyphosate-tolerant *Bacillus aryabhattai* strain CAP53 (NRRL No. B-50945).

46. An inoculum of claim 27, wherein the bacteria in the bacterial culture comprise *Bacillus thuringiensis* strain BT013A.

47. A plant seed of claim 28, wherein the bacteria in the bacterial culture comprise *Bacillus thuringiensis* strain BT013A.

48. An inoculum of claim 27, wherein the bacteria in the bacterial culture comprise *Bacillus cereus* family member strain EE349.

49. A plant seed of claim 28, wherein the bacteria in the bacterial culture comprise *Bacillus cereus* family member strain EE349.

50. A plant seed of claim 28, wherein the bacteria in the bacterial culture comprise *Bacillus mycoides* strain BT155.

51. A plant seed of claim 28, wherein the bacteria in the bacterial culture comprise *Bacillus mycoides* strain EE118.

52. A plant seed of claim 28, wherein the bacteria in the bacterial culture comprise *Bacillus mycoides* strain EE141.

53. A plant seed of claim 28, wherein the bacteria in the bacterial culture comprise *Bacillus mycoides* strain BT46-3.

54. An inoculum of claim 27, wherein the bacterial in the bacterial culture comprise *Bacillus cereus* family member strain EE349 and the bacteria have a 16S ribosomal RNA sequence having at least about 99% sequence identity with the sequence of SEQ ID NO: 18.

55. A plant seed of claim 28, wherein the bacterial in the bacterial culture comprise *Bacillus cereus* family member strain EE349 and the bacteria have a 16S ribosomal RNA sequence having at least about 99% sequence identity with the sequence of SEQ ID NO: 18.

56. An inoculum of claim 27, wherein the agriculturally acceptable carrier comprises a dispersant, a surfactant, an additive, water, a thickener, an anti-caking agent, residue breakdown, a composting formulation, a granular application, diatomaceous earth, an oil, a coloring agent, a stabilizer, a preservative, a polymer, a coating, or a combination thereof.

57. An inoculum of claim 27, wherein the inoculum further comprises a fertilizer, a micronutrient fertilizer material, an insecticide, a herbicide, a plant growth amendment, a molluscicide, an algicide, an additional bacterial inoculant, a fungal inoculant, or a combination thereof.

58. A plant seed of claim 40, wherein the agriculturally acceptable carrier comprises the preservative.

* * * * *

UNITED STATES PATENT AND TRADEMARK OFFICE
CERTIFICATE OF CORRECTION

| | |
|---|---|
| PATENT NO. | : 10,555,532 B2 |
| APPLICATION NO. | : 14/775858 |
| DATED | : February 11, 2020 |
| INVENTOR(S) | : Thompson et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this
Tenth Day of January, 2023

Katherine Kelly Vidal
*Director of the United States Patent and Trademark Office*